United States Patent
Ye et al.

(10) Patent No.: US 10,759,803 B2
(45) Date of Patent: Sep. 1, 2020

(54) ASPARAGINE ENDOPEPTIDASE (AEP) INHIBITORS FOR MANAGING CANCER AND COMPOSITIONS RELATED THERETO

(71) Applicant: Emory University, Atlanta, GA (US)

(72) Inventors: Keqiang Ye, Lilburn, GA (US); Haian Fu, Decatur, GA (US); Yuhong Du, Atlanta, GA (US)

(73) Assignee: Emory University, Atlanta, GA (US)

( * ) Notice: Subject to any disclaimer, the term of this patent is extended or adjusted under 35 U.S.C. 154(b) by 186 days.

(21) Appl. No.: 15/303,481

(22) PCT Filed: Apr. 8, 2015

(86) PCT No.: PCT/US2015/024850
§ 371 (c)(1),
(2) Date: Oct. 11, 2016

(87) PCT Pub. No.: WO2015/157376
PCT Pub. Date: Oct. 15, 2015

(65) Prior Publication Data
US 2017/0166569 A1    Jun. 15, 2017

Related U.S. Application Data

(60) Provisional application No. 61/978,225, filed on Apr. 11, 2014.

(51) Int. Cl.
| | |
|---|---|
| C07D 473/06 | (2006.01) |
| A61K 45/06 | (2006.01) |
| A61K 31/4015 | (2006.01) |
| A61K 31/4168 | (2006.01) |
| A61K 31/433 | (2006.01) |
| A61K 31/47 | (2006.01) |
| A61K 31/496 | (2006.01) |
| A61K 31/519 | (2006.01) |
| A61K 31/522 | (2006.01) |
| A61K 31/5355 | (2006.01) |
| C07D 207/452 | (2006.01) |
| C07D 215/06 | (2006.01) |
| C07D 257/04 | (2006.01) |
| C07D 273/02 | (2006.01) |
| C07D 277/54 | (2006.01) |
| C07D 285/135 | (2006.01) |
| C07D 471/04 | (2006.01) |

(52) U.S. Cl.
CPC ........ *C07D 473/06* (2013.01); *A61K 31/4015* (2013.01); *A61K 31/4168* (2013.01); *A61K 31/433* (2013.01); *A61K 31/47* (2013.01); *A61K 31/496* (2013.01); *A61K 31/519* (2013.01); *A61K 31/522* (2013.01); *A61K 31/5355* (2013.01); *A61K 45/06* (2013.01); *C07D 207/452* (2013.01); *C07D 215/06* (2013.01); *C07D 257/04* (2013.01); *C07D 273/02* (2013.01); *C07D 277/54* (2013.01); *C07D 285/135* (2013.01); *C07D 471/04* (2013.01)

(58) Field of Classification Search
None
See application file for complete search history.

(56) References Cited

U.S. PATENT DOCUMENTS

2017/0029388 A1    2/2017  Ye

FOREIGN PATENT DOCUMENTS

| EP | 0520552 | 12/1992 |
|---|---|---|
| JP | 01299229 | * 12/1989 |

OTHER PUBLICATIONS

Yamazaki et al. Identification of phosphodiesterase-1 and 5 dual inhibitors by a ligand-based virtual screening optimized for lead evolution. Bioorg. Med. Chem. Lett. 16, pp. 1371-79 (2006).*
STN entry for CAS Reg. No. 331675-23-1, entry date Apr. 17, 2001.*
Breckenridge Pharmaceutical, Inc. Dyphylline/Guaifenesin Package Insert (Jan. 2011). Accessed at https://www.drugs.com/pro/dyphylline-and-guaifenesin-tablets.html on Sep. 21, 2017.*
Yamazaki et al. Bioorganic & Medicinal Chemistry Letters 16 (2006) 1371-1379 (Year: 2006).*
Blicke et al. Diuretics. III. 1,3-Dimethyl-9-alkyl-and 1,3,9-Trimethyl-8-alkylthioisoxanthines, J. Am. Chem. Soc., 1956, 78 (22), pp. 5857-5863.
Hayallah et al. Antitumor Activity of Some New 1,3,8-Trisubstituted Purine-2,6-Diones and 1,3,6-Trisubstituted Thiazolo[2,3-f]Purine-2,4-Diones, Bull. Pharm. Sci., Assiut University, vol. 31, Part 2, 2008, pp. 391-399.

(Continued)

Primary Examiner — Jeffrey S Lundgren
Assistant Examiner — Michael J Schmitt
(74) Attorney, Agent, or Firm — Emory Patent Group

(57) ABSTRACT

This disclosure relates to asparagine endopeptidase inhibitors for managing cancer and compositions related thereto. In certain embodiments, the asparagine endopeptidase inhibitors are substituted 3,7-dihydropurine-2,6-dione derivatives useful for treating or preventing metastasis, tumor growth, and/or cancer. In certain embodiments, the disclosure relates to pharmaceutical compositions comprising an asparagine endopeptidase inhibitor and a pharmaceutically acceptable excipient. In certain embodiments, the disclosure relates to methods of treating a cancer comprising administering an effective amount of pharmaceutical composition a asparagine endopeptidase inhibitor disclosed herein to a subject in need thereof.

3 Claims, 12 Drawing Sheets

(56) References Cited

OTHER PUBLICATIONS

Lin et al. Functional Role of Asparaginyl Endopeptidase Ubiquitination by TRAF6 in Tumor Invasion and Metastasis, UNCI J Natl Cancer Inst (2014) 106(4): dju012.
Luo et al. Identification of BRAF Inhibitors through In Silico Screening J. Med. Chem. 2008, 51, 6121-6127.
Rogozin et al. Inhibitory effects of caffeine analogues on neoplastic transformation: structure-activity relationship, Carcinogenesis vol. 29 No. 6 pp. 1228-1234, 2008.
Romerosa et al. Biologically Active Platinum Complexes Containing 8-Thiotheophylline and 8-(Methylthio)theophylline, Inorg. Chem. 2004, 43, 905-913.

* cited by examiner

| Compound | AEP (μM) | Cathepsin-S (μM) | Cathepsin-L (μM) | Caspase-3 (μM) | Caspase-8 (μM) |
|---|---|---|---|---|---|
| BB1 | 0.13 ± 0.09 | > 200 | 5.66 ± 0.36 | > 200 | 28.71 ± 11.24 |
| 22 | 0.21 ± 0.01 | > 100 | > 100 | > 100 | > 100 |
| 31 | 0.26 ± 0.03 | > 100 | 1.30 ± 0.39 | > 100 | > 100 |
| 12 | 0.28 ± 0.02 | > 200 | > 200 | > 200 | > 200 |
| 38 | 0.37 ± 0.06 | > 200 | > 200 | 29.72 ± 4.68 | 76.11 ± 8.12 |
| 11 | 0.70 ± 0.18 | > 200 | > 200 | 31.86 ± 1.94 | 86.71 ± 10.31 |
| 10 | 0.71 ± 0.05 | > 200 | 3.79 ± 0.29 | 44.55 ± 5.01 | > 200 |
| 64 | 2.37 ± 0.10 | > 100 | > 100 | 15.39 ± 7.04 | > 100 |

A

B

C

ASPARAGINE ENDOPEPTIDASE (AEP) INHIBITORS FOR MANAGING CANCER AND COMPOSITIONS RELATED THERETO

CROSS-REFERENCE TO RELATED APPLICATIONS

This application is the National Stage of International Application Number PCT/US2015/024850 filed Apr. 8, 2015, which claims the benefit of priority to U.S. Provisional Application No. 61/978,225 filed Apr. 11, 2014. The entirety of each of these applications is hereby incorporated by reference for all purposes.

ACKNOWLEDGEMENT

This invention was made with government support under Grant RO1NS045627 awarded by the National Institutes of Health. The Government has certain rights in the invention.

BACKGROUND

Asparagine endopeptidase (AEP), also known as legumain, is a lysosomal cysteine protease that cleaves peptide bonds C-terminally to asparagine residues. AEP is involved in various cellular events, including antigen processing, the cleavage of other lysosomal enzymes, osteoclast formation, and proper kidney functionality. In mammals, AEP is highly expressed in the kidneys; mice deficient in AEP accumulate various proteins in the endosomes and lysosomes of the proximal tubule cells of their kidneys, which results in a pathology consisting of hyperplasia, fibrosis and glomerular cysts. AEP-null mice exhibit symptoms similar to those of hemophagocytic lymphohistiocytosis, suggesting the enzyme is involved in the pathophysiology of this disease. Biochemically, the enzyme is highly regulated by its specificity for asparagine residues and pH. The particular motif that AEP uses to recognize its substrates is not completely understood. Dysregulated AEP activity has been implicated in various diseases, including cancers and neurodegeneration.

Ovat et al. report aza-peptidyl Michael acceptor and epoxide inhibitors as inhibitors of *Schistosoma mansoni* and ixodes ricinus legumains (asparaginyl endopeptidases). See J Med Chem, 2009, 52, 7192-7210.

Loak et al. report acyloxymethylketone inhibitors of asparaginyl endopeptidase. See Biol Chem, 2003, 384, 1239-1246.

Niestroj et al. report inhibition of mammalian legumain by Michael acceptors and AzaAsn-halomethylketones. See Biol Chem (2002) 383, 1205-1214.

Xiang et al. report DNA vaccines target the tumor vasculature and microenvironment and suppress tumor growth and metastasis. See Immunol Rev, 2008, 222, 117-128.

Cancer cell metastasis is a complex process that involves the tumor microenvironment, which is a contributor to the increased invasiveness and migratory character of neoplastic cells. Malignant cells typically interact with a surrounding ecosystem of cells, including myeloid cells, fibroblasts, tumor-associated macrophages, and endothelial cells, to promote angiogenesis, degradation of the extracellular matrix and cell motility. Throughout tumor progression, many extracellular proteases contribute to the changes that occur in the tumor microenvironment and those most commonly associated with aberrant proliferation and metastasis are the matrix metalloproteinases (MMPs). The zinc-dependent endopeptidases are involved in a variety of cellular processes, including cell signaling, tissue remodeling, organ development and inflammatory response. However, the capability of this enzyme family to degrade the extracellular matrix has implications in cancer cell invasion and metastasis.

Asparagine Endopeptidase (AEP, Legumain) activates MMP-2 (Progelatinase A) by proteolytic removal of an N-terminal propeptide. AEP is a lysosomal cysteine endoprotease and is the mammalian enzyme that cleaves C terminally to asparagine residues. While only a limited quantity of AEP is detected in normal tissues, the enzyme is overexpressed on the cell surface and in cytoplasmic vesicles of solid tumors. The endoprotease activity of AEP has been associated with increased invasive and aggressive behavior of several cancers, including breast, prostate, colorectal and gastric carcinomas. See Gawenda et al., Legumain expression as a prognostic factor in breast cancer patients, Breast Cancer Res Treat, 2007, 102, 1-6; Ohno et al., Association of legumain expression pattern with prostate cancer invasiveness and aggressiveness, World J Urol, 2013, 31, 359-364; Li et al., Effects of legumain as a potential prognostic factor on gastric cancers, Med Oncol, 2013, 30, 621. Haugen et al., Nuclear legumain activity in colorectal cancer, PLoS One, 2013, 8, e52980. Thus, AEP inhibitors represent a promising cancer therapeutic.

Liao et al. report a targeting ligand for nanotherapeutic drug delivery inhibiting tumor growth. Nanomedicine, 2011, 7, 665-673.

References cited herein are not an admission of prior art.

SUMMARY

This disclosure relates to asparagine endopeptidase inhibitors for managing cancer and compositions related thereto. In certain embodiments, the asparagine endopeptidase inhibitors are substituted 3,7-dihydropurine-2,6-dione derivatives useful for treating or preventing metastasis, tumor growth, and/or cancer. In certain embodiments, the disclosure relates to pharmaceutical compositions comprising an asparagine endopeptidase inhibitor and a pharmaceutically acceptable excipient. In certain embodiments, the disclosure relates to methods of treating a cancer comprising administering an effective amount of pharmaceutical composition a asparagine endopeptidase inhibitor disclosed herein to a subject in need thereof.

DETAILED DISCUSSION

Figure 1:
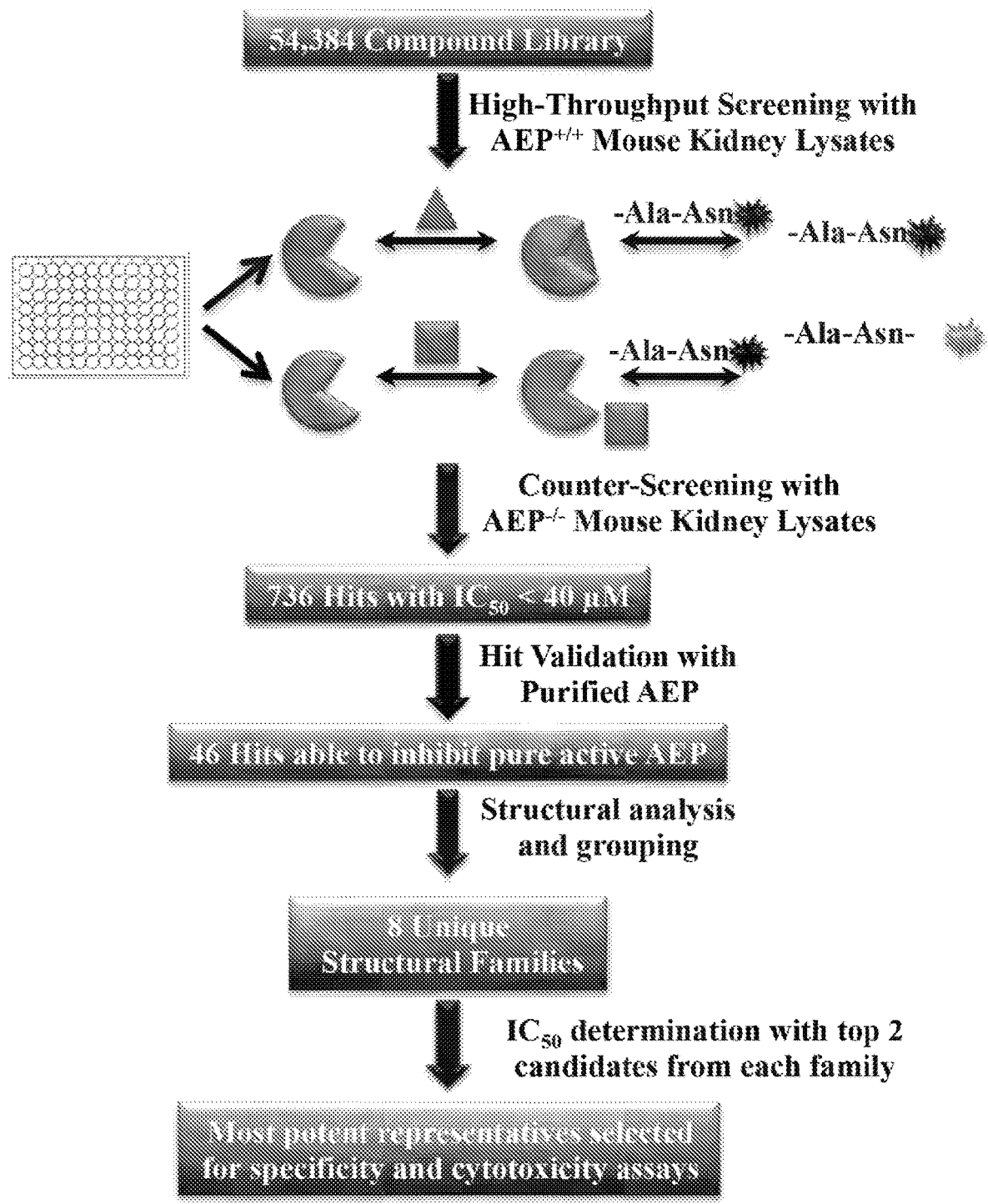
FIG. 1 illustrates a high-throughput screening scheme. An Asinex library of 54,384 compounds was screened with mouse kidney lysates, then counter-screened with AEP knock-out lysates to yield 736 hits with $IC_{50}$ values less than or equal to 40 μM. The hits were validated further with purified human AEP, and promising compounds were categorized into 8 groups. Compounds from each group were tested and the cytotoxicity and specificity were determined.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

TERMS

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

As used herein, the term "combination with" when used to describe administration with an additional treatment means that the agent may be administered prior to, together with, or after the additional treatment, or a combination thereof.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom or replacing an amino group with a hydroxy group. Contemplated derivative include switching carbocyclic, aromatic or phenyl rings with heterocyclic rings or switching heterocyclic rings with carbocyclic, aromatic or phenyl rings, typically of the same ring size. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze, all hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxy, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like. "Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH$_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—CH$_3$).

"Alkanoyl" refers to an alkyl as defined above attached through a carbonyl bridge (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfamoyl" refers to an alkyl as defined above attached through a sulfamoyl bridge (i.e., —S(=O)$_2$NHalkyl), and an "Arylsulfamoyl" refers to an alkyl attached through a sulfamoyl bridge (i.e., —S(=O)$_2$NHaryl).

"Alkylsulfinyl" refers to an alkyl as defined above with the indicated number of carbon atoms attached through a sulfinyl bridge (i.e. —S(=O)alkyl).

The terms "halogen" and "halo" refer to fluorine, chlorine, bromine, and iodine.

The term "aroyl" refers to an aryl group (which may be optionally substituted as described above) linked to a carbonyl group (e.g., —C(O)-aryl).

The term "sulfamoyl" refers to the amide of sulfonic acid (i.e, —S(=O)$_2$NRR')

An unspecified "R" group may be a hydrogen, lower alkyl, aryl, or heteroaryl, which may be optionally substituted with one or more, the same or different, substituents.

Throughout the specification, groups and substituents thereof may be chosen to provide stable moieties and compounds.

Blockade of Asparagine Endopeptidase Inhibits Cancer Metastasis

Asparagine endopeptidase (AEP), also called legumain, is highly expressed in various solid tumors, promoting cancer cell invasion, migration and metastasis. It has been proposed to be a prognostic marker and therapeutic target for cancer treatment. However, an effective non-peptide, small molecule inhibitor against this protease has not yet been identified. A family of xanthine derivatives selectively inhibit AEP, but not other related cysteine proteases, and suppress matrix metalloproteinases (MMP) cleavage, leading to the inhibition of cancer metastasis. Using high throughput screening, we identified several skeletal small molecules that specifically inhibit AEP. Data herein indicates that the compound (38D-21) represses breast cancer invasion and migration. Chronic treatment of nude mice, which had been inoculated with MDA-MB-231 cells, with inhibitor 38D-21 via oral administration inhibits breast cancer lung metastasis in a dose-dependent manner. This indicates that 38D-21 is a specific AEP inhibitor useful for cancer treatment.

Figure 12:
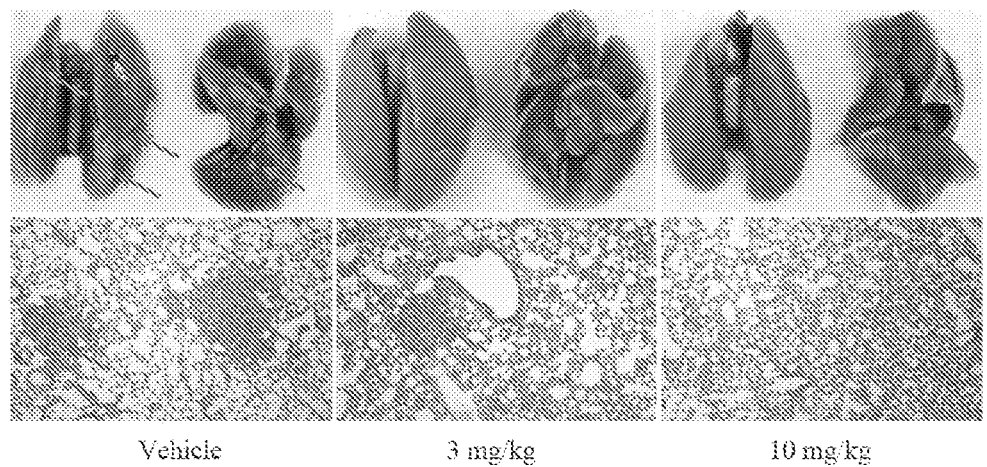
FIG. 12A-C shows data indicating compound 38D-21 prevents breast-to-lung metastasis in vivo. A. Representative lungs of mice treated with vehicle control, 3 mg/kg or 10 mg/kg compound 38D-21. Bottom panel depicts IHC staining. B. Quantification of metastasized cancer nodules found on the treated and untreated mouse lungs demonstrates that significantly less nodules are present in the lungs of the drug-treated mice. C. The proportion of mice exhibiting metastatic nodules decreased as the drug treatment dosage increased. For vehicle treated animals, metastasis was observed in 6/6 animals, whereas it only occurred in 2/6 for the animals treated with 3 mg/kg and 1/6 treated with 10 mg/kg.
Figure 12:
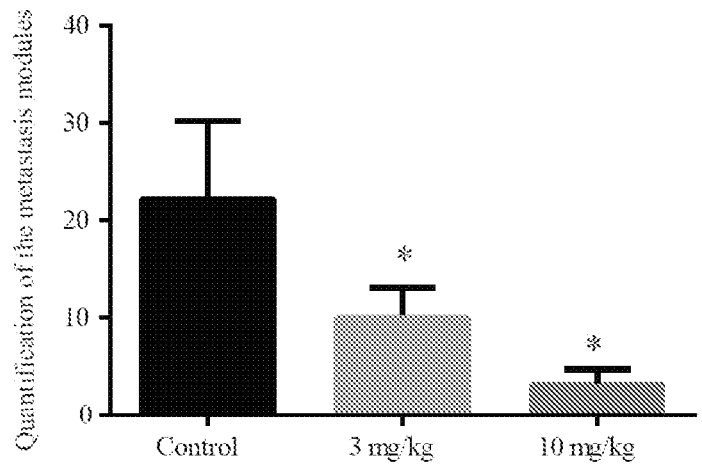
Figure 12:
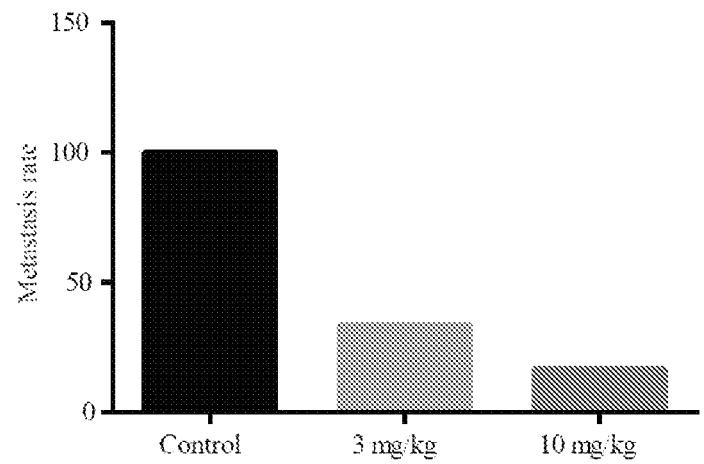

SAR analysis revealed that the R1 and R7 positions of compound 38 tolerate chemical substitution. Compound 38 and its derivatives may inhibit AEP by forming a disulfide bond between the inhibitor and cysteine 189 (C189), a key residue in AEP involved in hydrolyzing its substrates. Through the SAR analysis, several derivatives were shown, which display higher Caco-2 permeability, indicating augmented oral absorption. Biochemically, the AEP inhibitors robustly inhibit MMP-2 cleavage by AEP, leading to suppression of cancer cell migration and invasion. Accordingly, oral administration of identified AEP inhibitor represses breast cancer cell metastasis in an animal model, in a dose-dependent manner. Consequently, MMP-2 cleavage in tumor tissues is also-inhibited, indicating that the AEP inhibitor is orally bioactive. Chronic treatment of the animals with this inhibitor did not demonstrate prominent toxicity, as CBC (complete blood count), pathological examination and body weight demonstrate undetectable toxicity, though the spleen is slightly enlarged (FIG. 12). AEP-null mice display hepatosplenomegaly in which the weight of both liver and spleen is significantly higher than that of wild-type mice. The augmented spleen contains numerous hemophagocytes and immature myeloid lineage cells. However, blockade of AEP with its small molecular inhibitor did not elicit the same phenotypes in the spleen or liver. The bone marrow in AEP-null mice is also infiltrated with many enlarged histiocytes, but we did not observe a similar phenomenon in drug-treated mice, supporting that inhibition of AEP with its inhibitor alone may not be sufficient to provoke the defects observed in AEP knockout mice.

The aberrant expression of AEP in cancer cells and on the surface of tumor-associated macrophages has been linked to the enzyme's involvement in tumor development and metastasis. Lin et al., Selective ablation of tumor-associated macrophages suppresses metastasis and angiogenesis, Cancer Sci, 2013, 104, 1217-1225. There is evidence suggesting that AEP is a viable drug target and a biomarker for the diagnosis and progression of various cancers. Recent studies suggest that legumain expression could be a prognostic factor in patients with colorectal cancer, breast cancer, and ovarian cancer as well as a potential target for tumor therapy. Although peptide-based AEP-targeted prodrugs have been generated to specifically target common cancer drugs to cancer cells, no small molecular AEP inhibitors have been reported. Compound 38D-21 has favorable ADME and toxicity characteristics. The inhibitor was also found to inhibit the migration and invasion of MDA-MB-231 and MDA-MB-435 breast cancer cells in vitro. This is consistent with a previous report which showed that AEP does not affect the proliferation of SGC7901 human gastric cancer cells. Li et al., Effects of legumain as a potential prognostic factor on gastric cancers, Med Oncol, 2013, 30, 621. The efficacious inhibition of mammary tumor metastasis exhibited by compound 38D-21, suggests that AEP inhibitors would be successful in containing a primary tumor in its original environment and preventing the spread of tumorous tissues to more vital tissues. Thus, the AEP inhibitor can be utilized in conjunction with other known cancer therapeutics to eradicate the tumor at the primary site and simultaneously prevent the migration of the tumor cells to a secondary site.

There have been reports of peptide-based AEP inactivators that, when conjugated to a nanoparticle and the anticancer compound, doxorubicin, are able to specifically target doxorubicin to cancer cells, mitigating any systemic toxicity. In this case, the AEP inhibitor is used as a targeting molecule to direct the cancer drug specifically to cancer cells by exploiting the fact that AEP is extracellularly expressed on tumors and in tumor microenvironments; interestingly, the inhibitor conjugated nanoparticle alone is not sufficient to significantly decrease the size of the primary tumor. Liu et al., Targeting cell surface alpha(v)beta(3) integrin increases therapeutic efficacies of a legumain protease-activated auristatin prodrug, 2012, Mol Pharm 9, 168-175 and Liao et al., Synthetic enzyme inhibitor: a novel targeting ligand for nanotherapeutic drug delivery inhibiting tumor growth without systemic toxicity, Nanomedicine, 2011, 7, 665-673. The oral bioavailability 38D-21 make it advantageous in conjunction with other orally bioavailable anticancer agents, such as the breast cancer drug, lapatinib, which would decrease the discomfort of drug administration to cancer patients and concomitantly protect them from the formation of metastatic lesions. In certain embodiments, the disclosure contemplates conjugating a AEP inhibitor disclosed herein to an anticancer agent or cytotoxin, and uses of these conjugates to treat or prevent cancer.

Figure 13:
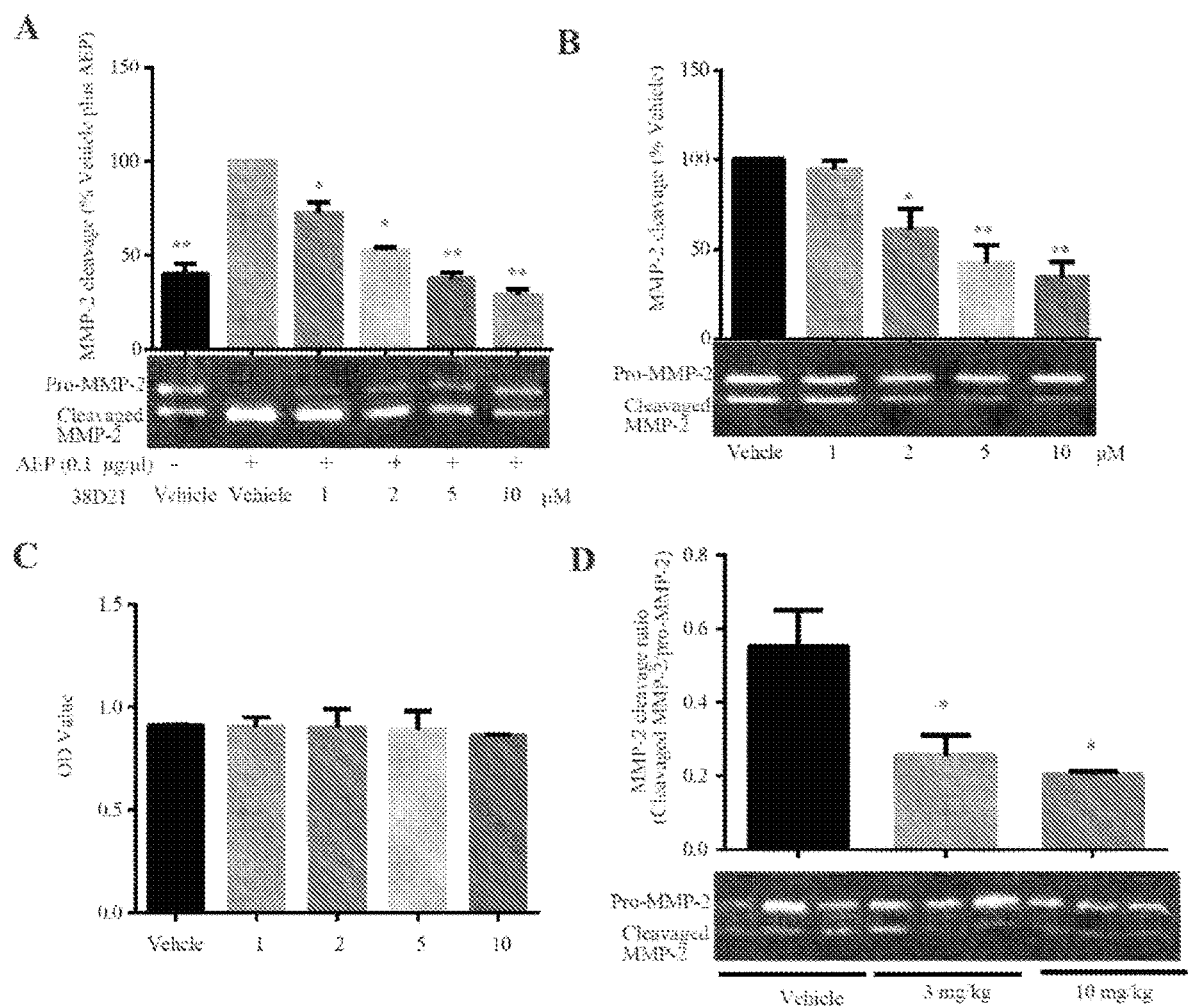
FIG. 13A-D shows data indicating compound 38D-21 inhibits AEP cleavage of MMP-2 in vitro and in vivo. A. Gelatin zymography was used to demonstrate that in the presence of AEP, MMP-2 is cleaved when only vehicle control is added to the reaction. In the presence of only 1 µM compound 38D-21, there is a significant decrease in the observed cleavage of MMP-2 and at the highest drug dose, 10 µM, MMP-2 cleavage returns to basal levels, as observed in the absence of AEP. B. Compound 38D-21 was administered to MDA-MB-231 cells and the inhibition of endogenous MMP-2 cleavage was observed in the presence of 1, 2, 5 and 10 µM compound. C. The cell viability was not affected by the drug dosages used in the experiment. D. The ratio of cleaved MMP-2 to full length MMP-2 (pro-MMP-2) significantly decreased in drug-treated mammary tumor tissue.

Although it is not intended that certain embodiments of this disclosure be limited by any particular mechanism, AEP inhibitors are likely imparting its effects by inhibiting the cleavage and activation of MMP-2 (FIG. 13). The matrix metalloproteinase is a known substrate of AEP, which cleaves a propeptide from the N-terminus of MMP-2, thus enabling the enzyme to degrade the extracellular matrix and promote more aggressive and invasive tumor growth. There is an overexpression of MMPs in the majority of human cancers, which is associated with an increase in invasive and metastatic behavior and an overall poor prognosis, since patients overexpressing these enzymes tend to have shorter survival rates. Additionally, in gastric cancer, the enhanced expression of MMP-2 has been most strongly correlated with a poor prognosis in comparison to any of the other MMPs.

MMP-2 cleavage in MDA-MB-231 cells and mammary tissue was inhibited by compound 38D-21 in a dose-dependent manner (FIG. 13), suggesting that the AEP inhibitor successfully regulates the activity of MMP-2. Legumain could degrade fibronectin, the main component of extracellular matrix. Conceivably, inhibition of AEP by inhibitors may potently block the breast-to-lung metastasis in mice. Therefore, an approach to prevent breast tumor metastasis is through the attenuation of MMP-2 activity by precluding its activation through the inhibition of AEP. Experiments reported herein indicate that one may prevent cancer metastasis and proliferation in different types of cancer, in which other AEP substrates are overexpressed.

Asparagine Endopeptidase Inhibitors

This disclosure relates to asparagine endopeptidase inhibitors. In certain embodiments, asparagine endopeptidase inhibitors are substituted 3,7-dihydropurine-2,6-dione derivatives. In some embodiments, the substituted 3,7-dihydropurine-2,6-dione derivative is a compound of the following formula:

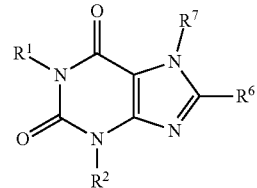

prodrugs, derivatives, or salts thereof wherein, $R^1$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^1$ is optionally substituted with one or more, the same or different, $R^{10}$;

$R^{10}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{10}$ is optionally substituted with one or more, the same or different, $R^{11}$;

$R^{11}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^2$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^2$ is optionally substituted with one or more, the same or different, $R^{20}$;

$R^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{20}$ is optionally substituted with one or more, the same or different, $R^{21}$;

$R^{21}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^6$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^6$ is optionally substituted with one or more, the same or different, $R^{60}$;

$R^{60}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{60}$ is optionally substituted with one or more, the same or different, $R^{61}$;

$R^{61}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^7$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^7$ is optionally substituted with one or more, the same or different, $R^{70}$;

$R^{70}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{70}$ is optionally substituted with one or more, the same or different, $R^{71}$; and $R^{71}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, $R^1$ is alkyl.

In certain embodiments, $R^2$ is alkyl.

In certain embodiments, $R^6$ is mercapto.

In certain embodiments, $R^7$ is alkyl.

In certain embodiments, the substituted 3,7-dihydropurine-2,6-dione derivatives selected from 1-ethyl-8-mercapto-3,7-dimethyl-3,7-dihydro-1H-purine-2,6-dione;

8-mercapto-1,3,7-trimethyl-3,7-dihydro-1H-purine-2,6-dione; and 1-benzyl-8-mercapto-3,7-dimethyl-3,7-dihydro-1H-purine-2,6-dione.

In some embodiments, the asparagine endopeptidase inhibitor is a substituted benzo[c][1,2,5]oxadiazole derivative such as a compound of the following formula:

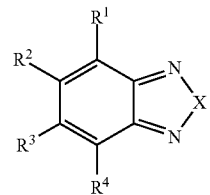

prodrugs, esters, derivatives, or salts thereof wherein,

X is O or S;

$R^1$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^1$ is optionally substituted with one or more, the same or different, $R^{10}$;

$R^{10}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{10}$ is optionally substituted with one or more, the same or different, $R^{11}$;

$R^{11}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^2$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^2$ is optionally substituted with one or more, the same or different, $R^{20}$;

$R^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{20}$ is optionally substituted with one or more, the same or different, $R^{21}$;

$R^{21}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^3$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^3$ is optionally substituted with one or more, the same or different, $R^{30}$;

$R^{30}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{30}$ is optionally substituted with one or more, the same or different, $R^{31}$;

$R^{31}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^4$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^4$ is optionally substituted with one or more, the same or different, $R^{40}$;

$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$; and $R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, $R^1$ is amino. In certain embodiments, $R^2$ is hydrogen. In certain embodiments, $R^3$ is hydrogen. In certain embodiments, $R^4$ is heterocycyl.

In some embodiments, the asparagine endopeptidase inhibitor is a substituted 1,3,4-thiadiazole derivative such as a compound of the following formula:

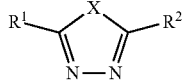

prodrugs, esters, derivatives, or salts thereof wherein,
X is O or S;
$R^1$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^1$ is optionally substituted with one or more, the same or different, $R^{10}$;

$R^{10}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{10}$ is optionally substituted with one or more, the same or different, $R^{11}$;

$R^{11}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^2$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^2$ is optionally substituted with one or more, the same or different, $R^{20}$;

$R^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{20}$ is optionally substituted with one or more, the same or different, $R^{21}$; and $R^{21}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, $R^1$ is mercapto. In certain embodiments, $R^2$ is amino.

In some embodiments, the asparagine endopeptidase inhibitor is a substituted 1-phenyl-1H-pyrrole-2,5-dione derivative such as a compound of the following formula:

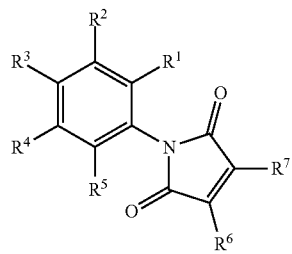

prodrugs, esters, derivatives, or salts thereof wherein,
$R^1$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^1$ is optionally substituted with one or more, the same or different, $R^{10}$;

$R^{10}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{10}$ is optionally substituted with one or more, the same or different, $R^{11}$;

$R^{11}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^2$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^2$ is optionally substituted with one or more, the same or different, $R^{20}$;

$R^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{20}$ is optionally substituted with one or more, the same or different, $R^{21}$;

$R^{21}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^3$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^3$ is optionally substituted with one or more, the same or different, $R^{30}$;

$R^{30}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{30}$ is optionally substituted with one or more, the same or different, $R^{31}$;

$R^{31}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^4$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^4$ is optionally substituted with one or more, the same or different, $R^{40}$;

$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;

$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^5$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{50}$ is optionally substituted with one or more, the same or different, $R^{51}$;

$R^{51}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^6$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^6$ is optionally substituted with one or more, the same or different, $R^{60}$;

$R^{60}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{60}$ is optionally substituted with one or more, the same or different, $R^{61}$;

$R^{61}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^7$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^7$ is optionally substituted with one or more, the same or different, $R^{70}$;

$R^{70}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{70}$ is optionally substituted with one or more, the same or different, $R^{71}$; and $R^{71}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In some embodiments, the asparagine endopeptidase inhibitor is a substituted 1-methylpiperazine derivative such as a compound of the following formula:

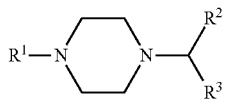

prodrugs, esters, derivatives, or salts thereof wherein, $R^1$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^1$ is optionally substituted with one or more, the same or different, $R^{10}$;

$R^{10}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{10}$ is optionally substituted with one or more, the same or different, $R^{11}$;

$R^{11}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^2$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^2$ is optionally substituted with one or more, the same or different, $R^{20}$;

$R^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{20}$ is optionally substituted with one or more, the same or different, $R^{21}$;

$R^{21}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^3$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^3$ is optionally substituted with one or more, the same or different, $R^{30}$;

$R^{30}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{30}$ is optionally substituted with one or more, the same or different, $R^{31}$; and $R^{31}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In some embodiments, the asparagine endopeptidase inhibitor is a substituted quinolin-5-ylmethanamine derivative such as a compound of the following formula:

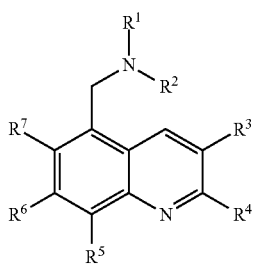

prodrugs, esters, derivatives, or salts thereof wherein, $R^1$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^1$ is optionally substituted with one or more, the same or different, $R^{10}$;

$R^{10}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{10}$ is optionally substituted with one or more, the same or different, $R^{11}$;

$R^{11}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^2$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^2$ is optionally substituted with one or more, the same or different, $R^{20}$;

$R^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{20}$ is optionally substituted with one or more, the same or different, $R^{21}$;

$R^{21}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^3$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^3$ is optionally substituted with one or more, the same or different, $R^{30}$;

$R^{30}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{30}$ is optionally substituted with one or more, the same or different, $R^{31}$;

$R^{31}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^4$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^4$ is optionally substituted with one or more, the same or different, $R^{40}$;

$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;

$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^5$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{50}$ is optionally substituted with one or more, the same or different, $R^{51}$;

$R^{51}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^6$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^6$ is optionally substituted with one or more, the same or different, $R^{60}$;

$R^{60}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{60}$ is optionally substituted with one or more, the same or different, $R^{61}$;

$R^{61}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^7$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^7$ is optionally substituted with one or more, the same or different, $R^{70}$;

$R^{70}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{70}$ is optionally substituted with one or more, the same or different, $R^{71}$; and $R^{71}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In some embodiments, the asparagine endopeptidase inhibitor is a substituted thiazole derivative such as a compound of the following formula:

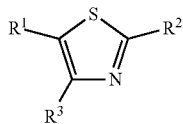

prodrugs, esters, derivatives, or salts thereof wherein, $R^1$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^1$ is optionally substituted with one or more, the same or different, $R^{10}$;

$R^{10}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{10}$ is optionally substituted with one or more, the same or different, $R^{11}$;

$R^{11}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^2$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^2$ is optionally substituted with one or more, the same or different, $R^{20}$;

$R^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{20}$ is optionally substituted with one or more, the same or different, $R^{21}$;

$R^{21}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^3$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^3$ is optionally substituted with one or more, the same or different, $R^{30}$;

$R^{30}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{30}$ is optionally substituted with one or more, the same or different, $R^{31}$; and $R^{31}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In some embodiments, the asparagine endopeptidase inhibitor is a substituted 6-methyl-5,6,7,8-tetrahydropyrido[4,3-d]pyrimidin-4(3H)-one derivative such as a compound of the following formula:

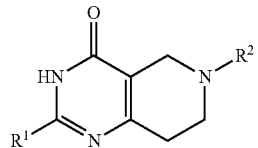

prodrugs, esters, derivatives, or salts thereof wherein, $R^1$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^1$ is optionally substituted with one or more, the same or different, $R^{10}$;

$R^{10}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{10}$ is optionally substituted with one or more, the same or different, $R^{11}$;

$R^{11}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^2$ is selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^2$ is optionally substituted with one or more, the same or different, $R^{20}$;

$R^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{20}$ is optionally substituted with one or more, the same or different, $R^{21}$; and $R^{21}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

PHARMACEUTICAL COMPOSITIONS

In certain embodiments, the disclosure relates to pharmaceutical compositions comprising a compound disclosed herein and a pharmaceutically acceptable excipient. In certain embodiments, the pharmaceutical composition is in the form of a pill, capsule, tablet, or saline aqueous buffer. In certain embodiments, the pharmaceutically acceptable excipient is selected from a saccharide, disaccharide, sucrose, lactose, glucose, mannitol, sorbitol, polysaccharides, starch, cellulose, microcrystalline cellulose, cellulose ether, hydroxypropyl cellulose (HPC), xylitol, sorbitol, maltito, gelatin, polyvinylpyrrolidone (PVP), polyethylene glycol (PEG), hydroxypropyl methylcellulose (HPMC), crosslinked sodium carboxymethyl cellulose, dibasic calcium phosphate, calcium carbonate, stearic acid, magnesium stearate, talc, magnesium carbonate, silica, vitamin A, vitamin E, vitamin C, retinyl palmitate, selenium, cysteine, methionine, citric acid, and sodium citrate, methyl paraben, propyl paraben, and combinations thereof.

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When the compounds of the disclosure contain a hydrogen-donating heteroatom (e.g. NH), the disclosure covers salts and/or isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug may include a covalently bonded carrier which releases the active parent drug when administered to a mammalian subject. Prodrugs may be prepared by modifying functional groups present in the compounds in such a way that the modifications are cleaved, either in routine manipulation or in vivo, to the parent compounds. Prodrugs include, for example, compounds wherein a hydroxy group is bonded to any group that, when administered to a mammalian subject, cleaves to form a free hydroxy group. Examples of prodrugs include, but are not limited to, acetate, formate and benzoate derivatives of alcohol functional groups in the compounds. Methods of structuring a compound as prodrugs may be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. It is well within the ordinary skill of the art to make an ester prodrug, e.g., acetyl ester of a free hydroxy group. It is well known that ester prodrugs are readily degraded in the body to release the corresponding alcohol. See e.g., Imai, Drug Metab Pharmacokinet. (2006) 21(3): 173-85, entitled "Human carboxylesterase isozymes: catalytic properties and rational drug design."

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds may be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

For an oral administration form, the compound may be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation may be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may contain other pharmaceutical auxiliaries such as surfactants, emulsifiers and stabilizers as well as a propellant.

For subcutaneous or intravenous administration, the compounds, if desired with the substances customary therefore such as solubilizers, emulsifiers or further auxiliaries are brought into solution, suspension, or emulsion. The compounds may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. When rectally administered in the form of suppositories, the formulations may be prepared by mixing the compounds with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions may be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethyl methacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the invention as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the invention in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein or compound delivery systems. Proteins and/or compounds may be entrapped in the poly (lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One may attach poly(ethylene glycol) to proteins (PEGylation) to increase the in vivo half-life of circulating therapeutic proteins and decrease the chance of an immune response.

Methods of Use

This disclosure relates to asparagine endopeptidase inhibitors useful for treating or preventing metastasis, tumor growth, and/or cancer. In certain embodiments, the disclosure relates to methods of treating a cancer comprising administering an effective amount of pharmaceutical composition comprising a compound disclosed herein to a subject in need thereof.

In certain embodiments, the subject is at risk of, exhibiting symptoms of, or diagnosed with breast cancer, prostate cancer, colorectal cancer, gastric cancer, lung cancer, skin cancer, bladder cancer, brain cancer, kidney cancer, endometrial cancer, pancreatic cancer, and thyroid cancer.

In certain embodiments, contemplated methods include further administering a second anti-cancer agent such as bevacizumab, gefitinib, erlotinib, temazolamide, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vincristine, vinblastine, vindesine, vinorelbine taxol, taxotere, etoposide, teniposide, amsacrine, topotecan, camptothecin, bortezomib, anegrilide, tamoxifen, toremifene, raloxifene, droloxifene, iodoxyfene fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, combretastatin, thalidomide, and/or lenalidomide or combinations thereof.

In certain embodiments, the disclosure contemplates treating or preventing breast cancer using compounds disclosed herein and one more other anti-cancer agents. In certain embodiments, the disclosure contemplates treating or preventing breast cancer using compounds disclosed herein and trastuzumab and/or lapatinib. In certain embodiments, the disclosure contemplates treating or preventing breast cancer using compounds disclosed herein and docetaxel and cyclophosphamide. In certain embodiments, the disclosure contemplates treating or preventing breast cancer using compounds disclosed herein and docetaxel, carboplatin, and trastuzumab. In certain embodiments, the disclosure contemplates treating or preventing breast cancer using compounds disclosed herein and cyclophosphamide, doxorubicin, and 5-fluorouracil (5-FU). In certain embodiments, the disclosure contemplates treating or preventing breast cancer using compounds disclosed herein and docetaxel, doxorubicin, and cyclophosphamide. In certain embodiments, the disclosure contemplates treating or preventing breast cancer using compounds disclosed herein and doxorubicin and cyclophosphamide followed by paclitaxel or docetaxel. In certain embodiments, the disclosure contemplates treating or preventing breast cancer using compounds disclosed herein and 5-FU, epirubicin, and cyclophosphamide followed by docetaxel or paclitaxel.

In certain embodiments, the disclosure contemplates treating or preventing prostate cancer using compounds disclosed herein and one more other anti-cancer agents. In certain embodiments, the disclosure contemplates treating or preventing prostate cancer using compounds disclosed herein and leuprolide, goserelin, or buserelin. In certain embodiments, the disclosure contemplates treating or preventing prostate cancer using compounds disclosed herein and flutamide, bicalutamide, enzalutamide, or nilutamide. In certain embodiments, the disclosure contemplates treating or preventing prostate cancer using compounds disclosed herein and ketoconazole or aminoglutethimide. In certain embodiments, the disclosure contemplates treating or preventing prostate cancer using compounds disclosed herein and abiraterone, bicalutamide, cabazitaxel, bicalutamide, degarelix, denosumab, docetaxel, enzalutamide, cabazitaxel, leuprolide, prednisone, denosumab, sipuleucel-T, or radium 223 dichloride and combinations thereof.

In certain embodiments, the disclosure contemplates treating or preventing colon cancer using compounds disclosed herein and one more other anti-cancer agents. In certain embodiments, the disclosure contemplates treating or preventing colon cancer using compounds disclosed herein and 5-FU, leucovorin, or capecitabine or combinations thereof. In certain embodiments, the disclosure contemplates treating or preventing colon cancer using compounds disclosed herein and capecitabine and oxaliplatin. In certain embodiments, the disclosure contemplates treating or preventing colon cancer using compounds disclosed herein and 5-FU, leucovorin, and oxaliplatin. In certain embodiments, the disclosure contemplates treating or preventing colon cancer using compounds disclosed herein and leucovorin, 5-FU, and irinotecan. In certain embodiments, the disclosure contemplates treating or preventing colon cancer using compounds disclosed herein and leucovorin, 5-FU, oxaliplatin, and irinotecan.

In certain embodiments, the disclosure contemplates treating or preventing colon cancer using compounds disclosed herein and bevacizumab or cetuximab. In certain embodiments, the disclosure contemplates treating or preventing colon cancer using compounds disclosed herein and 5-FU and leucovorin optionally with bevacizumab. In certain embodiments, the disclosure contemplates treating or preventing colon cancer using compounds disclosed herein and capecitabine optionally with bevacizumab. In certain embodiments, the disclosure contemplates treating or preventing colon cancer using compounds disclosed herein and irinotecan optionally with cetuximab. In certain embodiments, the disclosure contemplates treating or preventing colon cancer using compounds disclosed herein and cetuximab. In certain embodiments, the disclosure contemplates treating or preventing colon cancer using compounds disclosed herein and panitumumab. In certain embodiments, the disclosure contemplates treating or preventing colon cancer using compounds disclosed herein and regorafenib.

In certain embodiments, the disclosure contemplates treating or preventing lung cancer using compounds disclosed herein and a chemotherapy agent is selected from vinorelbine, etoposide, mitomycin C, gemcitabine, irinotecan, pemetrexed, gefitinib, erlotinib, lapatinib, crizotinib, and a vinca alkaloid or combinations thereof. In certain embodiments, the vinca alkaloid is vinblastine, vincristine, vindesine, or vinorelbine. In certain embodiments, the disclosure contemplates treating or preventing lung cancer using compounds disclosed herein and chemotherapy agent is bevacizumab panitumumab, zalutumumab, nimotuzumab, matuzumab, or cetuximab. In certain embodiments, the disclosure contemplates treating or preventing lung cancer using compounds disclosed herein and a platinum based agent and/or a taxane e.g., paclitaxel and docetaxel or combinations thereof.

In certain embodiments, the disclosure contemplates treating or preventing brain cancer, glioblastoma multiforme, oligodendroglioma, primitive neuroectodermal tumours, ependymomas, glioma comprising using compounds disclosed herein, e.g., 7-morpholinobenzo[c][1,2,5]oxadiazol-4-amine or optionally substituted derivative or salt thereof to a subject in need thereof. In certain embodiments, the compound is optionally administered in combination with temozolomide, procarbazine, carmustine (BCNU), lomustine (CCNU), vincristine, and combinations thereof. In certain embodiments, procarbazine, lomustine (CCNU) and vincristine are combined. In certain embodiments, the compound is optionally administered in combination with irinotecan, cis-platin, carboplatin, methotrexate, etoposide, bleomycin, vinblastine, actinomycin (Dactinomycin), cyclophosphamide, or ifosfamide.

In certain embodiments, the disclosure contemplates combinations of compounds disclosed herein with temozolomide. Treatment of glioblastoma includes chemotherapy during and after radiotherapy. On average, chemotherapy after surgery and radiotherapy can initially reduce the tumor size. The use of temozolomide both during radiotherapy and for six months post radiotherapy results in a significant increase in median survival with minimal additional toxicity. This treatment regime is now standard for most cases of glioblastoma where the patient is not enrolled in a clinical trial. Temozolomide seems to work by sensitizing the tumor cells to radiation. The U.S. Food and Drug Administration approved Avastin (bevacizumab) to treat patients with glioblastoma at progression after standard therapy.

In certain embodiments, the disclosure relates to administering compositions disclosed herein for the management of cancers or tumors in the brain by convection-enhanced delivery (CED). CED is a method of administrating compositions by direct infusion into the brain interstitial spaces utilizing a fluid pressure gradient after catheter placement.

The cancer treatments disclosed herein can be applied as a sole therapy or can involve, conventional surgery or radiotherapy or chemotherapy. Such chemotherapy can include one or more of the following categories of anti-tumor agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon (ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-Her2 antibody trastuzumab and the anti-epidermal growth factor receptor (EGFR) antibody, cetuximab), farnesyl transferase inhibitors, tyrosine kinase inhibitors and serine/threonine kinase inhibitors, for example inhibitors of the epidermal growth factor family for example EGFR family tyrosine kinase inhibitors such as: N-(3-chloro-4-fluorophenyl)-7-methoxy-6-(3-morpholinopropoxy)quinazolin-4-a mine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazolin-4-amine (CI 1033), for example inhibitors of the platelet-derived growth factor family and for example inhibitors of the hepatocyte growth factor family, for example inhibitors of phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (AbI) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin ocvβ3 function and angiostatin);

(vi) vascular damaging agents such as Combretastatin A4;

(vii) antisense therapies, for example those which are directed to the targets listed above, such as an anti-RAS antisense; and (viii) immunotherapy approaches, including for example ex-vivo and in-vivo approaches to increase the immunogenicity of subject tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies, and approaches using the immunomodulatory drugs thalidomide and lenalidomide [Revlimid®].

The combination therapy also contemplates use of the disclosed pharmaceutical compositions with radiation therapy or surgery, as an alternative, or a supplement, to a second therapeutic or chemotherapeutic agent.

In certain embodiments, the disclosure contemplates treating or preventing leukemia using compounds disclosed herein and a leukemia (CLL) chemotherapeutic plan. A typical chronic lymphocytic leukemia (CLL) chemotherapeutic plan includes combination chemotherapy with chlorambucil or cyclophosphamide, plus a corticosteroid such as prednisone or prednisolone. The use of a corticosteroid has the additional benefit of suppressing some related autoimmune diseases, such as immunohemolytic anemia or immune-mediated thrombocytopenia. In resistant cases, single-agent treatments with nucleoside drugs such as fludarabine, pentostatin, or cladribine may be successful. Patients may consider allogeneic or autologous bone marrow transplantation. In certain embodiments, the disclosure contemplates combination treatments using compounds disclosed herein in combination with chloroambucil, cyclophosphamide, prednisone, prednisolone, fludarabine, pentostatin, and/or cladribine or combinations thereof. Treatment of acute lymphoblastic leukemia typically includes chemotherapy to bring about bone marrow remission. Typical regiments include prednisone, vincristine, and an anthracycline drug, L-asparaginase or cyclophosphamide. Other options include prednisone, L-asparaginase, and vincristine. Consolidation therapy or intensification therapy to eliminate any remaining leukemia may include antimetabolite drugs such as methotrexate and 6-mercaptopurine (6-MP).

In certain embodiments, the disclosure contemplates combination treatments using compounds disclosed herein in combination with COP, CHOP, R-CHOP, imatinib, alemtuzumab, vincristine, L-asparaginase or cyclophosphamide, methotrexate and/or 6-mercaptopurine (6-MP). COP refers to a chemotherapy regimen used in the treatment of lymphoma of cyclophosphamide, vincristine, and prednisone or prednisolone and optionally hydroxydaunorubicin (CHOP) and optionally rituximab (R-CHOP).

EXPERIMENTAL

Inhibitors of AEP were Identified by High-Throughput Screen

Figure 2:
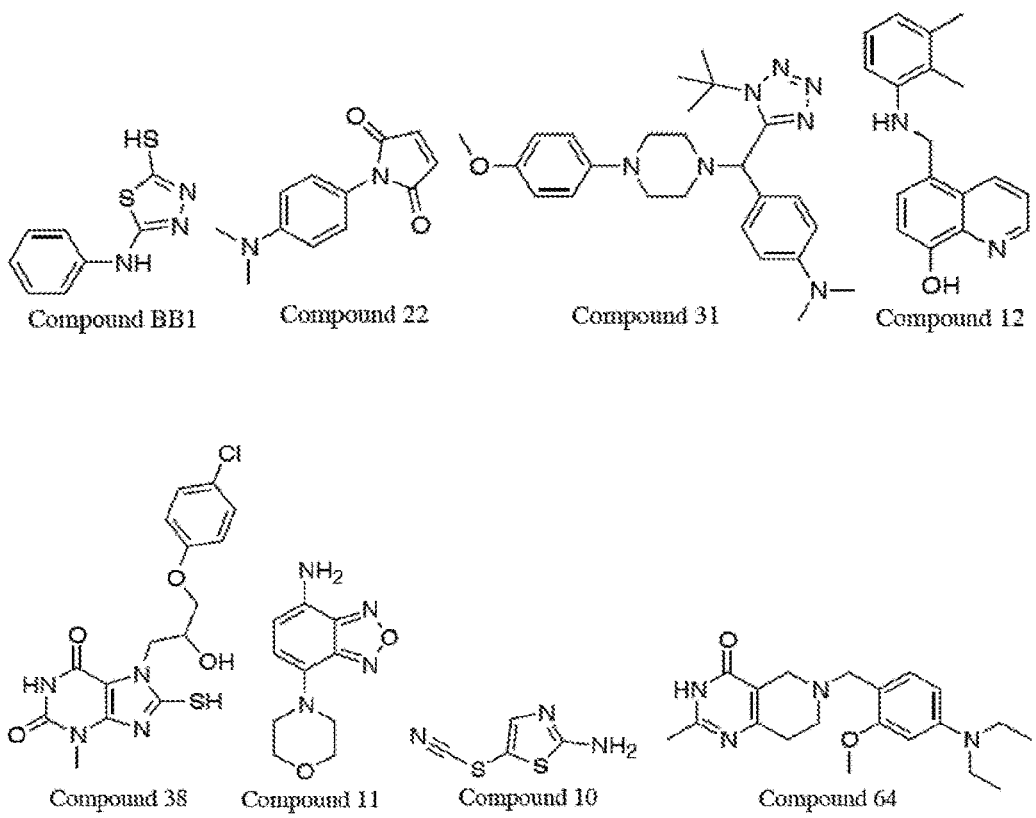
FIG. 2 shows data on the determination of IC50 values. Purified recombinant enzyme was incubated with various concentrations of inhibitor in appropriate assay buffers in the presence of increasing concentrations of inhibitor. The formation of fluorescent product was monitored in duplicate reactions and the data was fit to appropriate equations to calculate the $IC_{50}$ values.

To identify small-molecule inhibitors of AEP, a high-throughput screen was designed in conjunction with the Emory Chemical Biology Discovery Center. The screen incorporated mouse kidney lysates to assay a 54,384 compound library. Upon counter-screening with kidney lysates from AEP−/− mice, 736 hits were confirmed to display $IC_{50}$ values toward the cellular AEP less than or equal to 40 µM. A third screen with purified active AEP found that 46 hits exhibited promising inhibitory activity (FIG. 1). Additional structural analysis and grouping allowed the compounds to be sorted into 8 distinct backbone families. After some of the most potent compounds from each group were tested with purified active AEP, $IC_{50}$ values for the top 8 candidates were found. The specificity of the compounds was also determined using four major cysteine proteases (FIG. 2). Compound BB1 appeared to possess the greatest potency toward AEP, at about 130 nM, and it was about 38-fold more selective for AEP than Cathepsin-L. Compound 22 on the other hand, had an $IC_{50}$ greater than 100 µM for all of the tested cysteine proteases. Compounds 11 and 38 also seemed to be potent inhibitors of AEP, since they displayed $IC_{50}$ values of approximately 700 and 370 nM, respectively, and they were at least 80-fold more selective for AEP than Caspase-3 or Caspase-8. Compound 64 exhibited the highest $IC_{50}$ at 2.37 µM. It is a low-micromolar inhibitor and it is over 40-fold more selective for AEP as compared to Cathepsin-S, Cathepsin-L and Caspase-8, and about 6-fold more selective for Caspase-3.

Cell Permeability of the Compounds

Figure 3:
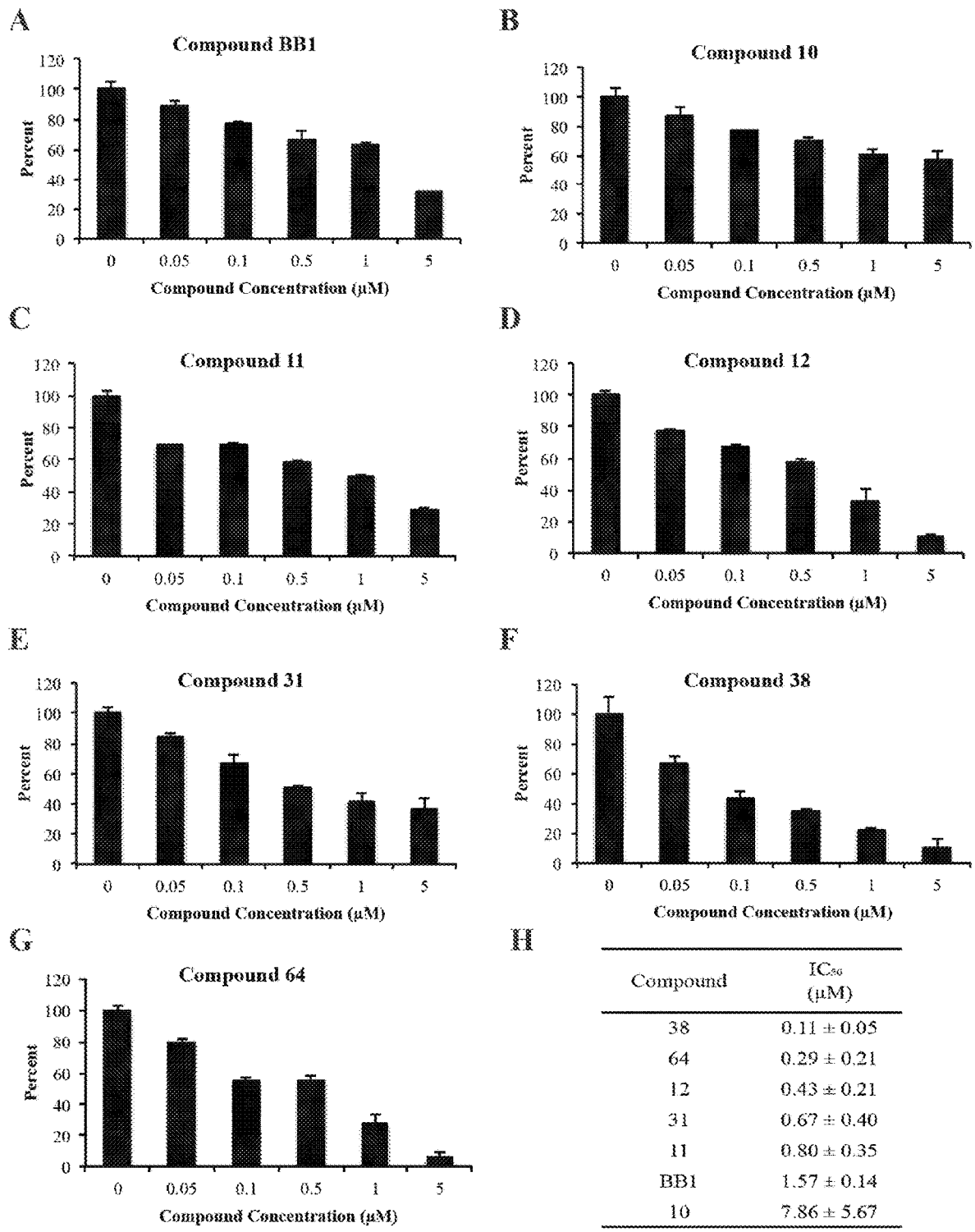
FIG. 3A-H shows data on the determination of $IC_{50}$ values in intact Pala cells. The cells were incubated with inhibitors for 2 hrs then cells washed, harvested and lysed and the residual enzymatic activity was determined. Lysate was normalized by Bradford assay and the experiment was performed in triplicate and the mean results and SEM were plotted.

In an attempt to assess the activity of the compounds in intact cells, the compounds were incubated with human B lymphoblastoid pala cells, which are rich in endogenous AEP and have been used for inhibiting AEP in cellular assay. Most of the compounds were able to inhibit the enzyme with $IC_{50}$ values in the sub-micromolar range, however compounds BB1 and 10 exhibited slightly larger $IC_{50}$ values; many of the compounds seem to be cell permeable (FIG. 3). ADME characteristics of compounds with $IC_{50}$ values<1 µM were further evaluated.

In Vitro ADMET Profiles

Figure 4:
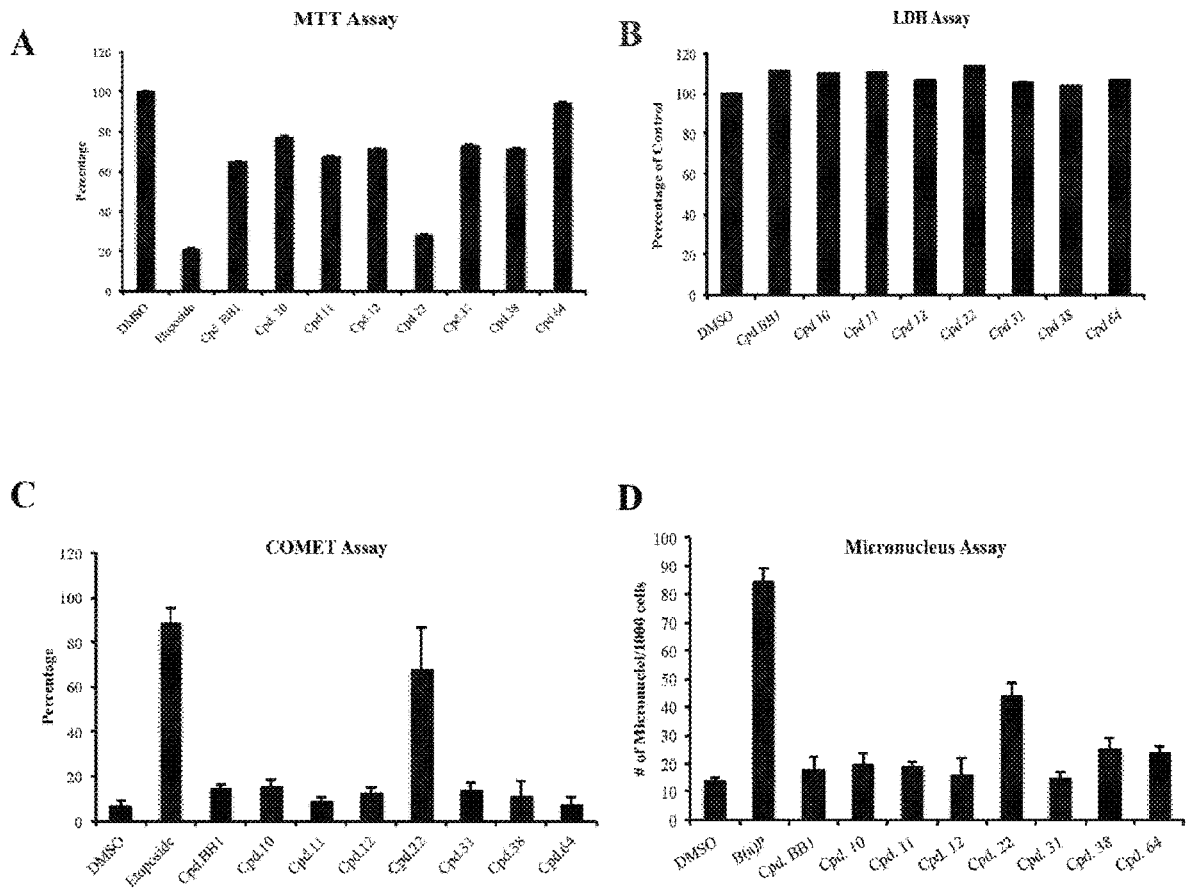
FIG. 4A-D shows data on cytotoxicity and genotoxicity of compounds. A. MTT assay, in which 50 µM of each compound was incubated with HepG2 cells for 24 hrs. The compound-containing medium was removed and the cells were incubated with MTT solution for 3 hrs. Subsequently, the MTT solution was replaced with DMSO and the $OD_{570}$ was observed. B. LDH assay, in which 50 µM of each compound was incubated with primary culture neurons for 48 hrs. The media was then collected and incubated with LDH assay substrate for 30 min at room temp, in the dark. After the reactions were quenched, the OD490 was observed. C. COMET assay results; 50 µM compound was incubated with HepG2 cells for 24 hrs. The cells were then added low-melt agarose and plated on microscope slides. The cells were lysed and the DNA was denatured and subject to electrophoresis. Finally, the DNA was stained with SYBR Green and 100 nuclei were counted for each sample, in each experiment; the experiment was performed in triplicate. D. Micronucleus assay results; 50 µM compound was incubated with HepG2 cells for 24 hrs. Cells were fixed and nuclei were stained with DAPI and 1,000 cells were counted per sample; three independent experiments were performed.
Figure 5:
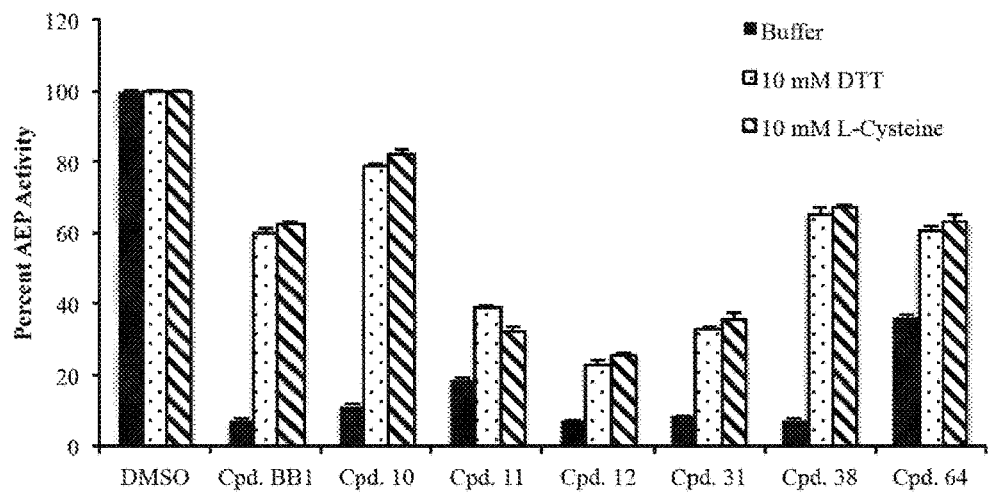
FIG. 5 shows data indicating DTT Reversibility. AEP was reacted with specified inhibitor, after 15 min 10 mM DTT or L-cysteine was added to the reaction and the fluorescent signal was read for an additional 15 min. At the end of the second 15 min incubation, the percentage of product formed in the presence of each compound was determined in comparison to the DMSO control reaction.

In an effort to characterize the toxicity of the compounds, an MTT assay was performed using human hepatocellular carcinoma, HepG2 cells and primary culture neurons to monitor the cell viability. In HepG2 cells, compound 22, the maleimide-containing derivative, revealed a similar toxicity to the positive control etoposide, which is a topoisomerase inhibitor and known to induce double strand breaks (FIG. 4A). The cytotoxicity of the compounds in primary neuronal cultures was determined using an LDH assay to measure cytolysis (FIG. 4B). The carcinogenicity of a compound is directly proportional to its induction of micronuclei. To assess whether compounds possess any carcinogenicity, a COMET assay was performed and a micronucleus assay. Benzo(α)pyrene (B(a)p) that generates measurable DNA nicks within these assays was included as a positive control. Following treatment for 24 hr with 50 μM compound, compound 22 was the only test compound to show genotoxicity, thus, it was excluded from further analyses (FIGS. 4C and 4D).

To explore the in vitro ADME profiles of the compounds, additional tests were conducted. A Caco-2 monolayer permeability screen was performed to assess the absorption characteristics of the compounds and compounds 11 and 31 were found to be highly permeable and should therefore be well physiologically absorbed (Table 1).

TABLE 1

Caco-2 permeability.

| Compound | A –>B $P_{app}$ ($10^{-6}$ cm · s$^{-1}$) | B –> A $P_{app}$ ($10^{-6}$ cm · s$^{-1}$) | $R_E$ |
|---|---|---|---|
| Ranitidine | 0.8 | 2.5 | 3.2 |
| Warfarin | 28.5 | 12.6 | 0.4 |
| Talinolol | 0.3 | 6.0 | 23.9 |
| 11 | 35.0 | 7.0 | 0.2 |
| 12 | 1.4 | 3.7 | 2.7 |
| 31 | 19.3 | 17.4 | 0.9 |
| 38 | 1.1 | 20.3 | 18.2 |
| 64 | <LLOQ | <LLOQ | NA |

LLOQ = Compound not detected on receiver side

In the BBB-PAMPA permeability assay, compound 11 was detected at high levels and was thus considered able to cross the blood-brain barrier (Table 2).

TABLE 2

BBB-PAMPA permeability.

| Compound | $P_e$ ($10^{-6}$ cm · s$^{-1}$) |
|---|---|
| Theophylline | 0.12 |
| Verapamil | 17.2 |
| 11 | >25 |
| 12 | <LLOQ |
| 31 | <LLOQ |
| 38 | 0.007 |
| 64 | ND |

LLOQ = Compound not detected on receiver side
ND = Peak not detected due to bioanalysis issue The human liver microsomal stability screen demonstrated that following 30 min of incubation, 76% of compound 11 and 88% of compound 38 remained in human liver microsomes (Table 3).

TABLE 3

Liver microsomal stability.

| Compound | Species | Mean Remaining Parent (with NADPH) | Mean Remaining Parent (NADPH-free) |
|---|---|---|---|
| Verapamil | Human | 4.6% | 101% |
|  | Mouse | 2.6% | 101% |
| Warfarin | Human | 96% | 104% |
|  | Mouse | 91% | 100% |
| 11 | Human | 76% | 93% |
|  | Mouse | 20% | 103% |
| 12 | Human | 1% | 1% |
|  | Mouse | 1% | 0% |
| 31 | Human | 12% | 75% |
|  | Mouse | 16% | 86% |
| 38 | Human | 88% | 107% |
|  | Mouse | 98% | 99% |
| 64 | Human | ND* | ND* |
|  | Mouse | ND* | ND* |

ND = Peak not detected due to bioanalysis issue (poor ionization)

According to CYP inhibition screening, compound 31 was able to inhibit CYP2C9 at 69.2% and CYP2C19 at 55.7%, while compound 64 inhibited CYP2D6 at 58.3% at 10 μM of concentration, suggesting that these two compounds can be capable of producing potential drug-drug interactions (Table 4).

TABLE 4

CYP inhibition.

| Compound | Test Concentration (μM) | CYP3A4-Midazolam | CYP3A-Testosterone | CYP2C9 | CYP2D6 | CYP2C19 | CYP1A2 |
|---|---|---|---|---|---|---|---|
| 11 | 10 | 8.0% | 21.6% | 5.6% | 21.9% | 6.8% | 37.0% |
|  | 3 | 3.6% | 4.1% | 4.3% | 7.8% | 4.4% | 13.1% |
| 12 | 10 | -2.5% | 27.6% | -2.7% | -2.6% | 29.4% | 44.5% |
|  | 3 | -2.5% | 14.2% | 4.3% | 2.9% | 13.4% | 28.4% |
| 31 | 10 | 18.1% | 0.7% | 69.2% | 1.4% | 55.7% | 10.3% |
|  | 3 | -0.9% | 2.5% | 47.8% | 9.9% | 37.7% | 13.5% |
| 38 | 10 | 10.4% | 2.4% | 17.1% | 0.9% | 9.5% | 10.5% |
|  | 3 | 7.3% | -6.0% | 15.6% | -5.4% | -12.0% | -7.6% |
| 64 | 10 | 10.1% | -0.1% | 7.9% | 58.3% | 20.4% | 22.2% |
|  | 3 | 0.6% | 1.5% | 4.6% | 34.6% | 31.6% | 73.7% |

DTT Reversibility of the Compounds

Although it is not intended that embodiments of this disclosure be limited by any particular mechanism, to gain additional insight into the mechanism utilized by the inhibitors for abrogation of AEP activity, their reversibility in the presence of free thiols was determined. The addition of a strong reducing agent, such as DTT, or a weaker reducing agent, L-cysteine, to an inhibited reaction can be used to out-compete the inhibitory agent and restore catalytic activity to an enzyme with an active-site thiol residue. Here, a similar approach was used by adding a reducing agent, either DTT or L-cysteine, to a reaction, in which AEP had been incubated with a specified inhibitor, in an attempt to reverse the effects of the inhibitor. The thiol-containing compounds, BB1 and 38, and compound 10, which contains a thiocyanate moiety, all appeared to have regained a substantial amount of activity in the presence of the reducing agents, indicating that the reducing agents were able to reduce the active-site cysteine of the enzyme and thus increase the effective concentration of active enzyme. However, in the presence of the sulfur-containing compounds, BB1, 10 and 38, AEP regained a substantial amount of activity. For compounds BB1 and 38, this increase in enzymatic activity may be due to the reduction of a disulfide linkage between the inhibitor and the enzyme, since these compounds contain thiols. Compound 10 contains a thiocyanate and may undergoes nucleophilic attack by the enzyme's active-site thiolate to form a thioimidate enzyme-inhibitor complex. Under acidic conditions, this complex is reducible by either a strong reducing agent, such as DTT, or the weaker L-cysteine. Thus, it is possible that compounds BB1, 10 and 38 may form covalent bonds with the active-site cysteine of AEP and competitively inhibit its activity.

Inhibitor Characterization

Figure 6:
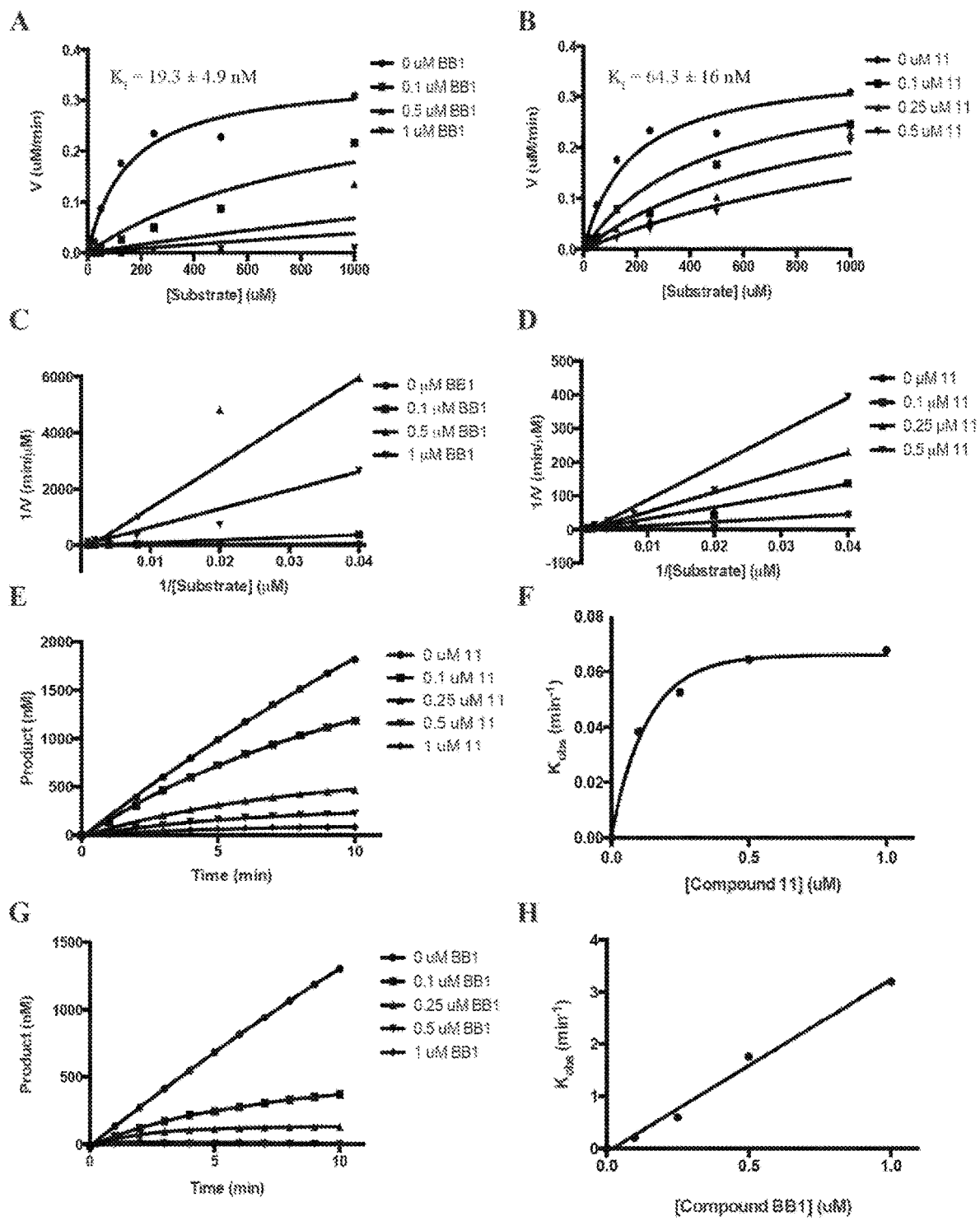
FIG. 6A-H shows data on competitive, slow-binding inhibitors of AEP. Steady-state kinetic parameters were determined from Michaelis-Menten plots, fit to a competitive inhibition equation, by varying substrate, Z-AAN-AMC, at fixed concentrations of: A. Compound 11 B. Compound BB1. KI values for each inhibitor were determined by global fits to the competitive inhibition equation. C. Time course inactivation assays were used to generate progress curves, depicting product formation as a function of time. Pseudo first-order rate constants were obtained at each concentration of compound 11. D. Re-plot of the pseudo first-order rate constants, $k_{obs}$, vs. the concentration of compound 11. E. Time course inactivation assays were used to generate progress curves, depicting product formation as a function of time. Pseudo first-order rate constants were obtained at each concentration of compound BB1. F. Re-plot of the pseudo first-order rate constants, $k_{obs}$, vs. the concentration of compound BB1.

To continue to assess the mechanism utilized by the compounds to inhibit AEP, the inhibition kinetics were determined for compound, 11, as well as compound BB1, in an attempt to confirm that the thiol moiety is competitively inhibiting the enzyme. In order to determine the mode of inhibition of compounds BB1 and 11, steady-state kinetic parameters were measured in the presence of increasing concentrations of each inhibitor (FIG. 6A-B). The resulting Michaelis-Menten plots for each compound seem be indicative of competitive inhibition. Competitive inhibitors compete with substrate for binding at the active site of the enzyme, thus at saturating substrate concentrations, inhibition can be attenuated. The inhibitor constant, $K_I$ is the concentration of inhibitor that produces half-maximal inhibition and is a measurement of an inhibitor's potency; the KI values for the compounds are listed in FIG. 6A-B. The Michaelis-Menten plots and the nanomolar-range inhibition constants of compounds BB1 and 11 indicates that they are potent competitive inhibitors of AEP. Since BB1 contains a thiol group, it can form a disulfide bond with the active-site cysteine of AEP. The reactive group of compound 11 remains unclear, so to characterize its mode of inhibition further, progress curves were measured at increasing concentrations of inhibitor. The resulting curvilinear plots indicate that compound 11 inhibits AEP in a time and concentration-dependent manner (FIG. 6C). Additionally, plotting the pseudo-first-order rate constants of inhibition, $k_{obs}$, which were determined from the progress curves, yielded a hyperbolic curve, consistent with a two-step mechanism of inactivation (FIG. 6D). The rate of inactivation, $k_{inact}$, was found to be 0.075±0.002 min$^{-1}$, thus the second-order rate constant, $k_{inact}/K_I$ is $1.2 \times 10^6$ min$^{-1} \cdot M^{-1}$ suggesting that compound 11 irreversibly inactivates AEP. Compound BB1 also displays the progress curves indicative of a slow-binding inhibitor (FIG. 6E). However, the $k_{obs}$ versus inhibitor concentration plot yielded a straight line, maybe due to the rapid disulfide formation reaction (FIG. 6F). The second-order rate constant of inhibition, $k_{inact}/K_I$, can be obtained from the slope of this curve and is $3.3 \times 10^6$ min$^{-1} \cdot M^{-1}$ and for compound BB1 indicating that this compound can form a disulfide linkage with the active-site thiol of AEP.

Efficacy in Cellular Models of Acidosis

Figure 7:
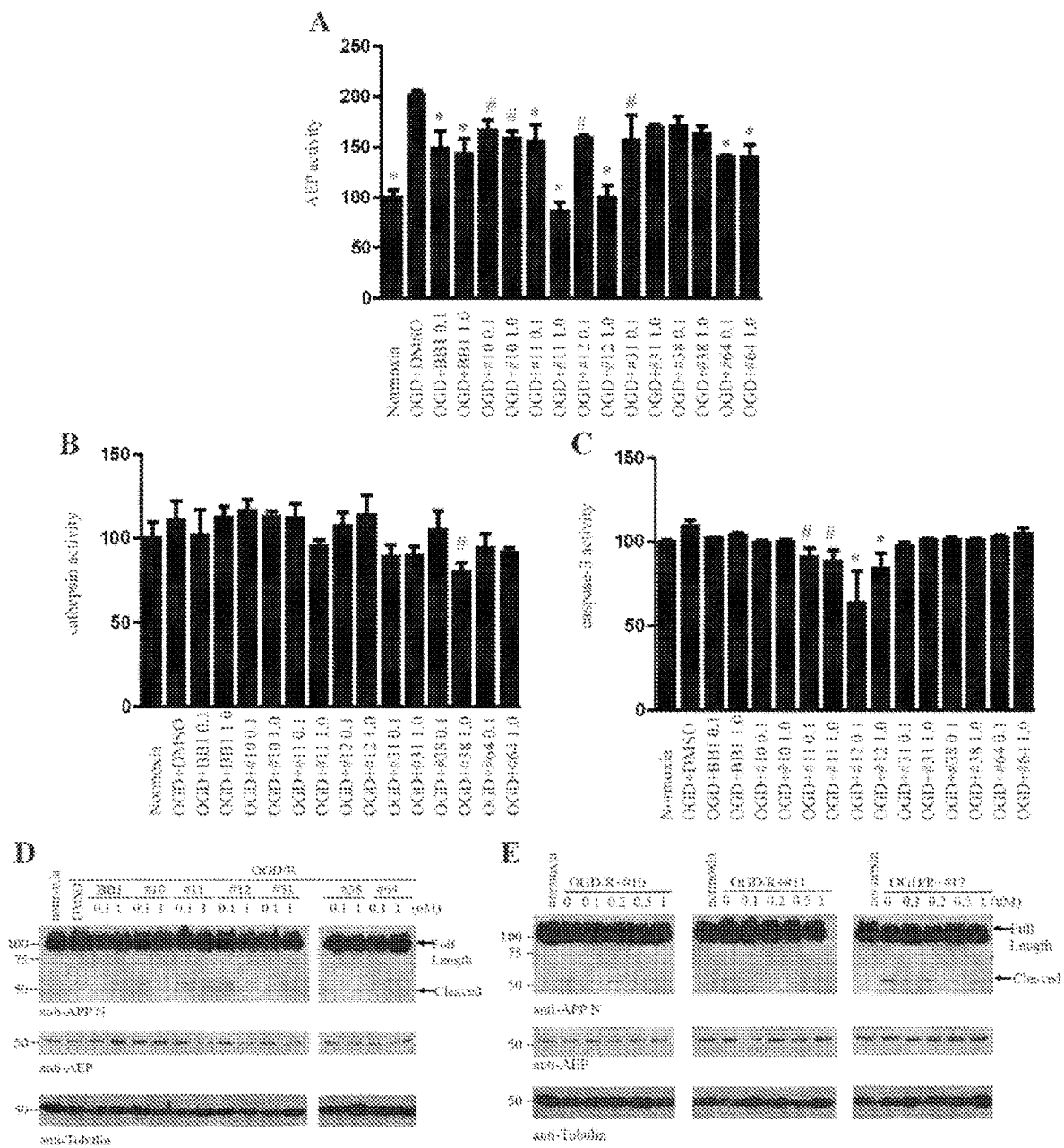
FIG. 7A-E shows data on the inhibition of AEP in OGD-treated neurons. A. AEP activity, measured in primary neuronal cultures with 5 µM Cbz-Ala-Ala-Asn-AMC (x-axis denotes neurons were treated with 0.1 µM or 1.0 µM specified compound). B. Caspase activity, measured in primary neuronal cultures with 5 µM Ac-Asp-Glu-Val-Asp-AMC. C. Cathepsin activity, measured in primary neuronal cultures with 5 µM D-Val-Leu-Lys-AMC. D. Inhibition of APP cleavage. Lysates of primary cortical neurons pre-incubated with compounds for 30 min, underwent OGD for 4 hrs, were reperfused for 18 hrs (normoxia neurons remained at normoxic conditions). E. APP can be cleaved in a dose-dependent manner. Lysates of primary cortical neurons pre-incubated with compounds for 30 min, underwent OGD for 4 hrs, were reperfused for 18 hrs (normoxia neurons remained at normoxic conditions).

Depriving cells of oxygen and glucose is a cellular model that is employed to trigger acidosis in cultured cells. The efficacy of the compounds in a cellular model of oxygen-glucose deprivation (OGD) was determined in an effort to mimic the effects of stroke in primary cultured neurons. As a result of depriving neurons of oxygen and glucose-containing medium, AEP activity was doubled (FIG. 7A, 'DMSO-Norm' compared to 'DMSO-OGD'), while Caspase-3 and Cathepsin activities remained relatively unchanged. In the presence of compound 11, there was a marked dose-dependent decrease in AEP activity, which was not observed for either Caspase-3 or Cathepsin. Compound 12 was also able to produce a slight decrease in AEP activity, selective to only that enzyme (FIG. 7). Since ischemia has been found to highly increase the risk of Alzheimer's Disease following stroke, the cleavage of the amyloid precursor protein (APP) was assess following OGD treatment (FIGS. 7D and E). Cleavage of APP is observed in response to only DMSO treatment (FIG. 7D, lane 2), and it appears that upon the treatment of 1 µM of compounds 10, 11, and 12, and just 0.1 µM of compound s31, 38 and 64, the cleavage was blocked, presumably due to AEP inhibition. FIG. 7E also shows a dose-dependent decrease of APP cleavage in response to the presence of compounds 10 and 12.

Compound 38 Inhibits AEP Activity

Figure 8:
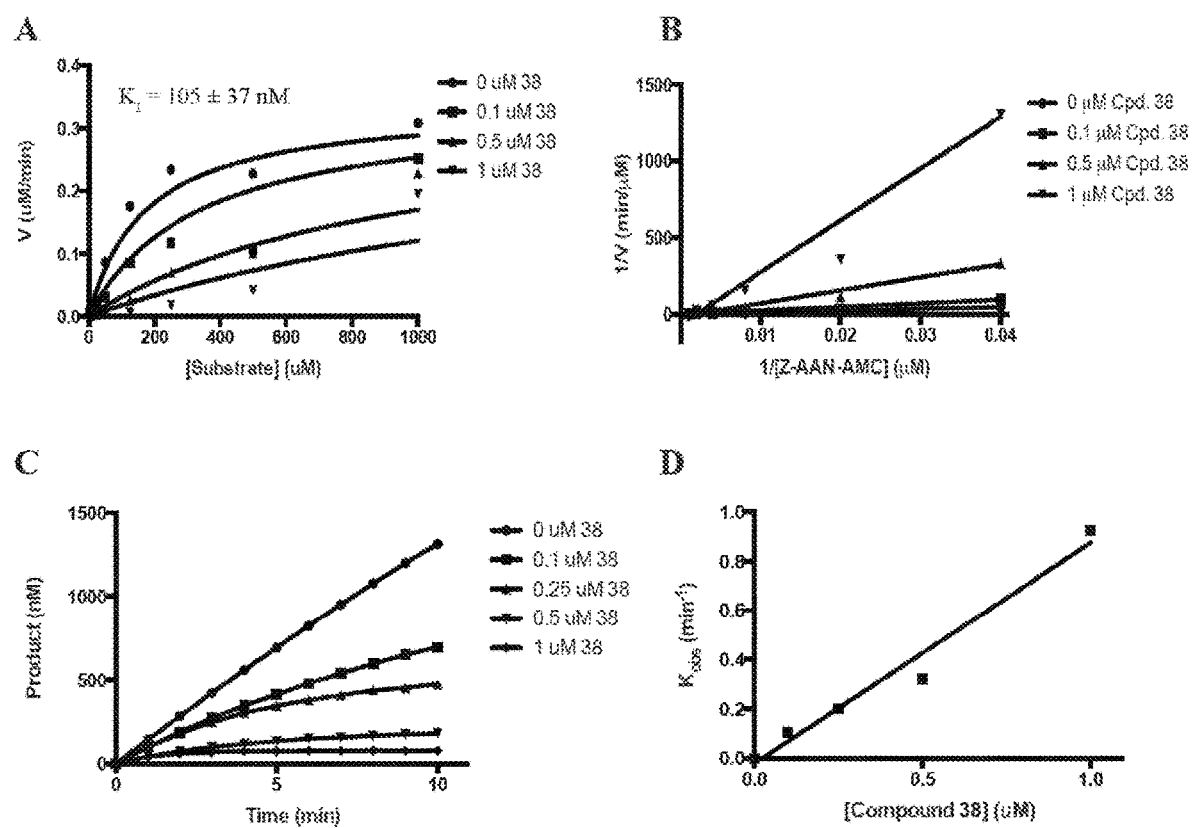
FIG. 8A-D shows data of kinetic analysis of compound 38 inhibition of AEP. A. Michaelis-Menten plots displaying competitive inhibition of AEP. The inhibition constant, $K_1$, was determined from the globally fit data. B. Double reciprocal Lineweaver-Burk plots also displaying competitive inhibition. C. Nonlinear progress curves obtained from the time course inactivation experiments, indicating that compound 38 is a slow-binding inhibitor of AEP. DC. A plot of the corrected $k_{obs}$ values obtained from each curve in (B) versus the concentration of compound 38, which enabled the calculation of the second-order rate constant, $k_{inact}/K_I$ to be determined to measure the potency of the inhibitor.

A kinetic analysis of the small molecule inhibitor demonstrated that compound 38 competitively inhibits AEP activity very strongly, KI=105±37 nM (FIGS. 8A & B). Time course inactivation assays produced nonlinear curves, indicating that the compound is a slow-binding inhibitor of AEP; the secondary plot of the rate constants against each inhibitor concentration demonstrates that AEP is inactivated rapidly and potently, as the second-order rate constant, kinact/$K_I$, for compound 38 is $8.9 \times 105$ min$^{-1} \cdot M^{-1}$ (FIGS. 8C & D).

Structure-Activity Relationship (SAR) Analysis of Compound 38

Figure 9:
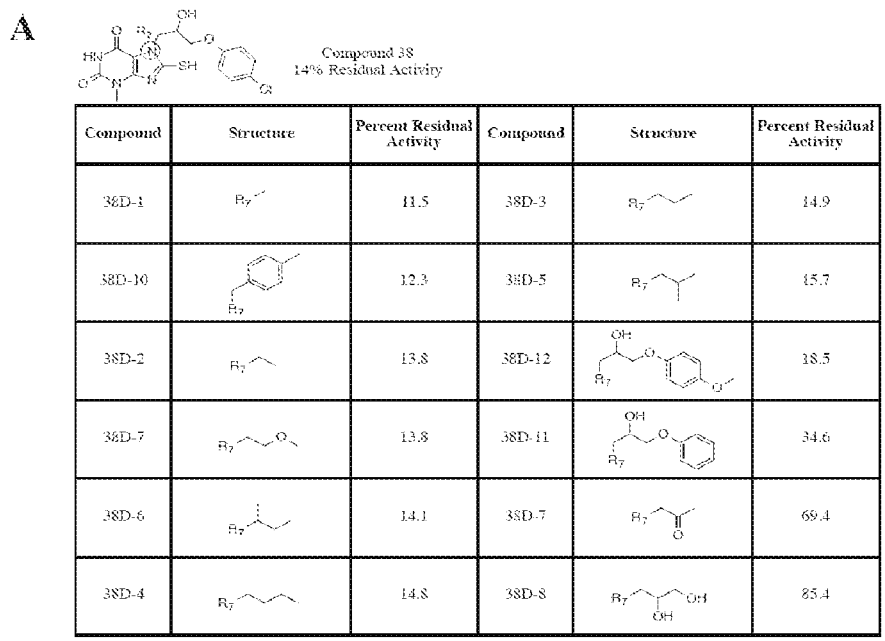
FIG. 9A-C shows the structures and data of an SAR analysis. A. The structures and percentages of residual AEP activity of derivatives, in which substitutions were made to the nitrogen in the R7 position. B. The structures and percentages of residual AEP activity of the compound 38 derivatives, in which substitutions were made to the nitrogens at the R7 and R1 positions. C. The structures and percentages of residual AEP activity of the compound 38 derivatives, in which substitutions were made at the R7, R1 and R6 position in xanthine ring.
Figure 9:
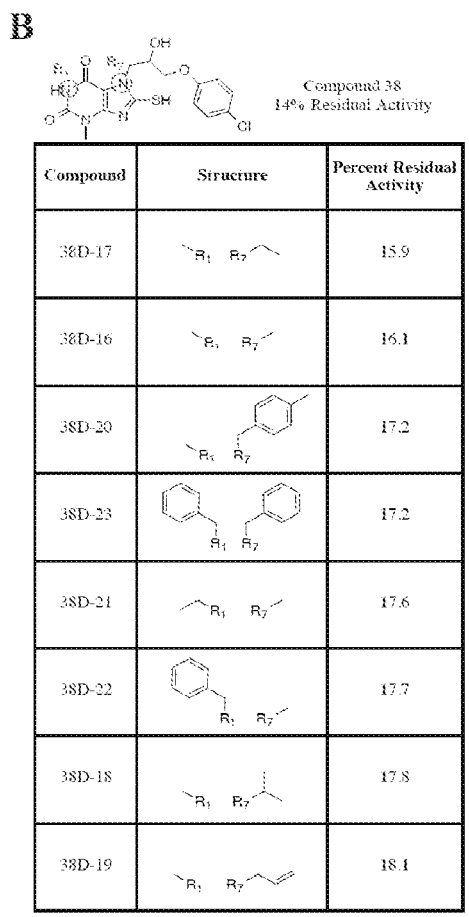
Figure 9:
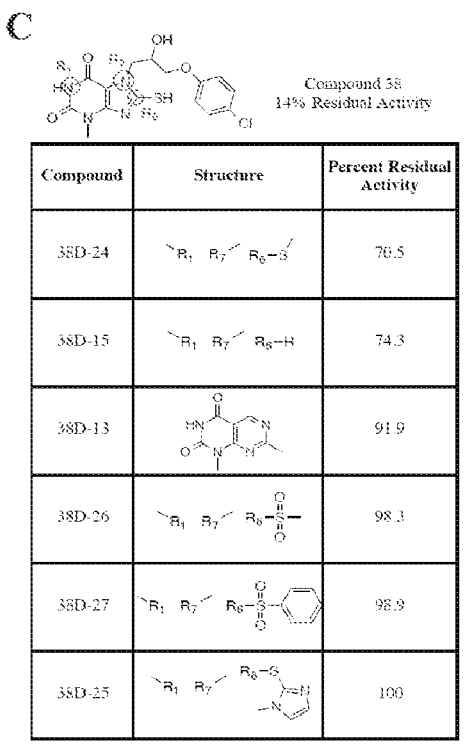

In an effort to improve the drug ability of the compound, structure-activity relationship studies were performed with various derivatives. Each compound was incubated with 50 nM purified, active AEP and 5 µM substrate peptide and the percentage of residual enzyme activity was calculated compared to a control reaction. FIG. 9 displays the results of this analysis. Substitution at the R7 position alone with smaller hydrophobic alkane chains did not seem to affect the activity of the parent molecule. Interestingly, compound 38D-12, which contains an electron-donating methoxy group in place of the chloride of the parent compound, has similar reactivity as compound 38, suggesting that the electron-withdrawing —Cl is not critical for the effective inhibition of AEP. However, there is greater than a two-fold loss in activity when nothing is placed in the para-position of the benzene ring, as in the case of compound 38D-11. There was also a 5-6-fold loss of activity of the parent compound, when a ketone or diol group was substituted at the R7 position, demonstrating that although some manipulations at this position can be tolerated, while others cannot (FIG. 9A).

Nonetheless, the simultaneous addition of a methyl or benzyl group at the nitrogen at R1 and substitution of a small alkyl group or a bulky benzene-containing group at R7 did not seem to have any deleterious effects on the compound's inhibitory activity (FIG. 9B). Conversely, the observed alterations made to the thiol group of compound 38 had effects on its inhibitory activity (FIG. 9C).

Compound 38D-21 Displays Potent Caco-2 Permeability and Inhibition Specificity

Three of the derivatives, 38D-16, 38D-21 and 38D-22, were chosen for further characterization. Caco-2 permeability assays revealed that the derivatives displayed much higher permeability than the parent compound 38.

| Caco-2 Permeability | | | |
| --- | --- | --- | --- |
| Compound | A ->B $P_{app}$ ($10^{-6}$ cm · $s^{-1}$) | B -> A $P_{app}$ ($10^{-6}$ cm · $s^{-1}$) | $R_E$ |
| Ranitidine | 0.2 | 1.3 | 8.1 |
| Warfarin | 35.5 | 8.6 | 0.2 |
| Talinolol | 0.3 | 5.4 | 16.8 |
| 38 | 1.1 | 20.3 | 18.2 |
| 38D-16 | 0.9 | 3.0 | 3.3 |
| 38D-21 | 2.7 | 7.0 | 2.6 |
| 38D-22 | 10.0 | 30.5 | 3.0 |

Figure 10:
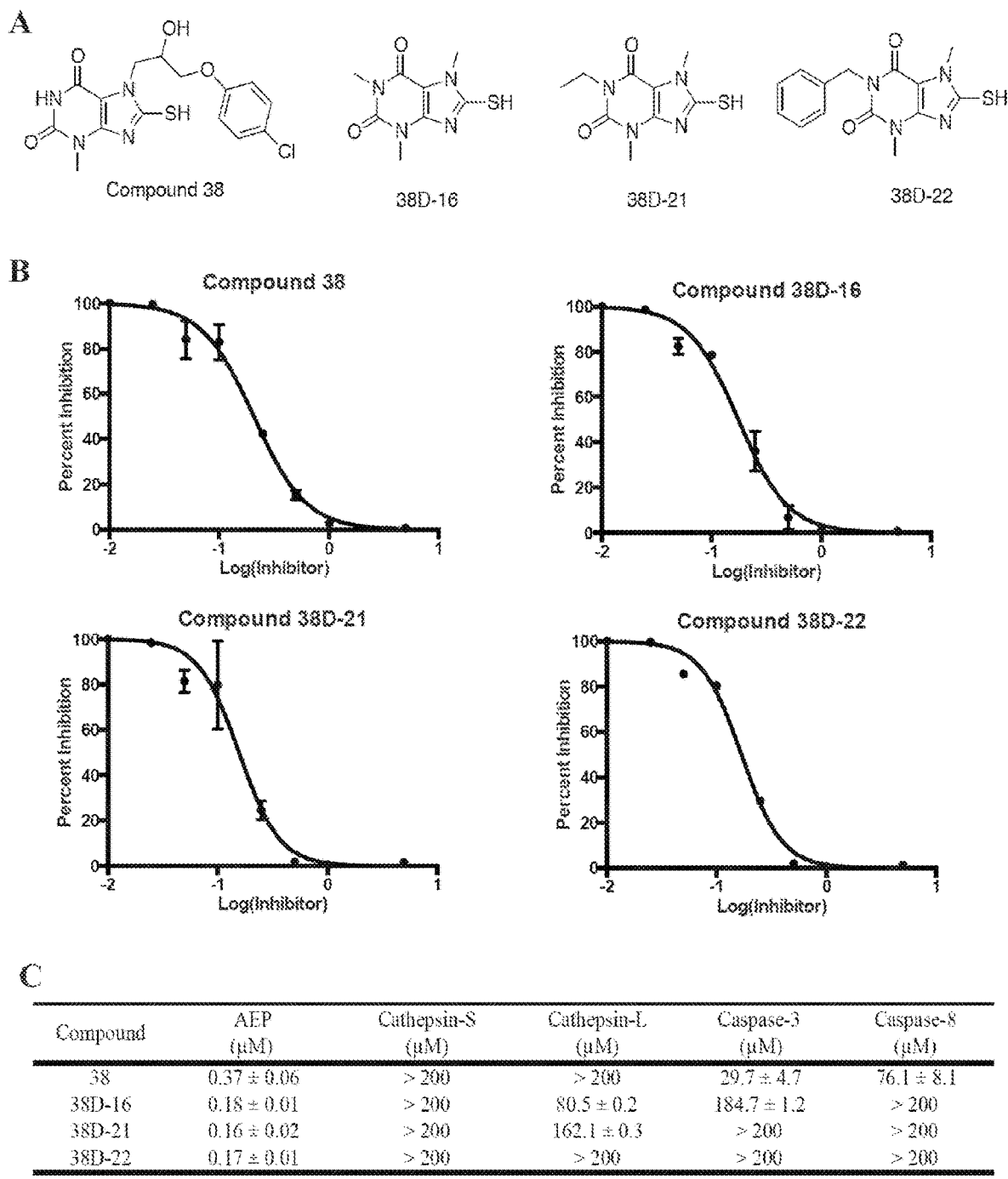
FIG. 10A-C shows data indicating compound 38D-21 specifically inhibits AEP. A. Structures of compound 38 and its derivatives with increased hydrophobicity. B. IC50 curves for compound 38 and its derivatives against pure AEP. C. Inhibition specificity assay. IC50 values of compound 38 and its derivatives against AEP and other related major Cysteine proteases.

Compound 38D-21 exhibited a favorable efflux: influx ratio. The inhibitory activity of the derivatives were also assessed in more depth to confirm their inhibitory potential. Inhibition assays revealed that they possess submicromolar $IC_{50}$ values, and that they inhibit AEP with about 2-fold increased potency compared to compound 38 (FIG. 10). The derivatives also have similar, and in some cases improved, selectivity for AEP over other major cysteine proteases. Compounds 38D-16, 38D-21 and 38D-22 have $IC_{50}$ values that are greater than 200 µM against Cathepsin-S (FIG. 10). Although compounds 38D16 and 38D-21 are able to inhibit Cathepsin-L, they inhibit AEP 500-fold and 1000-fold, respectively, more selectively. Some of the derivatives are less potent inhibitors of Caspase-3 and Caspase-8, and are therefore more specific for AEP as compared to compound 38.

Compound 38D-21 Inhibits Breast Cancer Cell Invasion In Vitro

Figure 11:
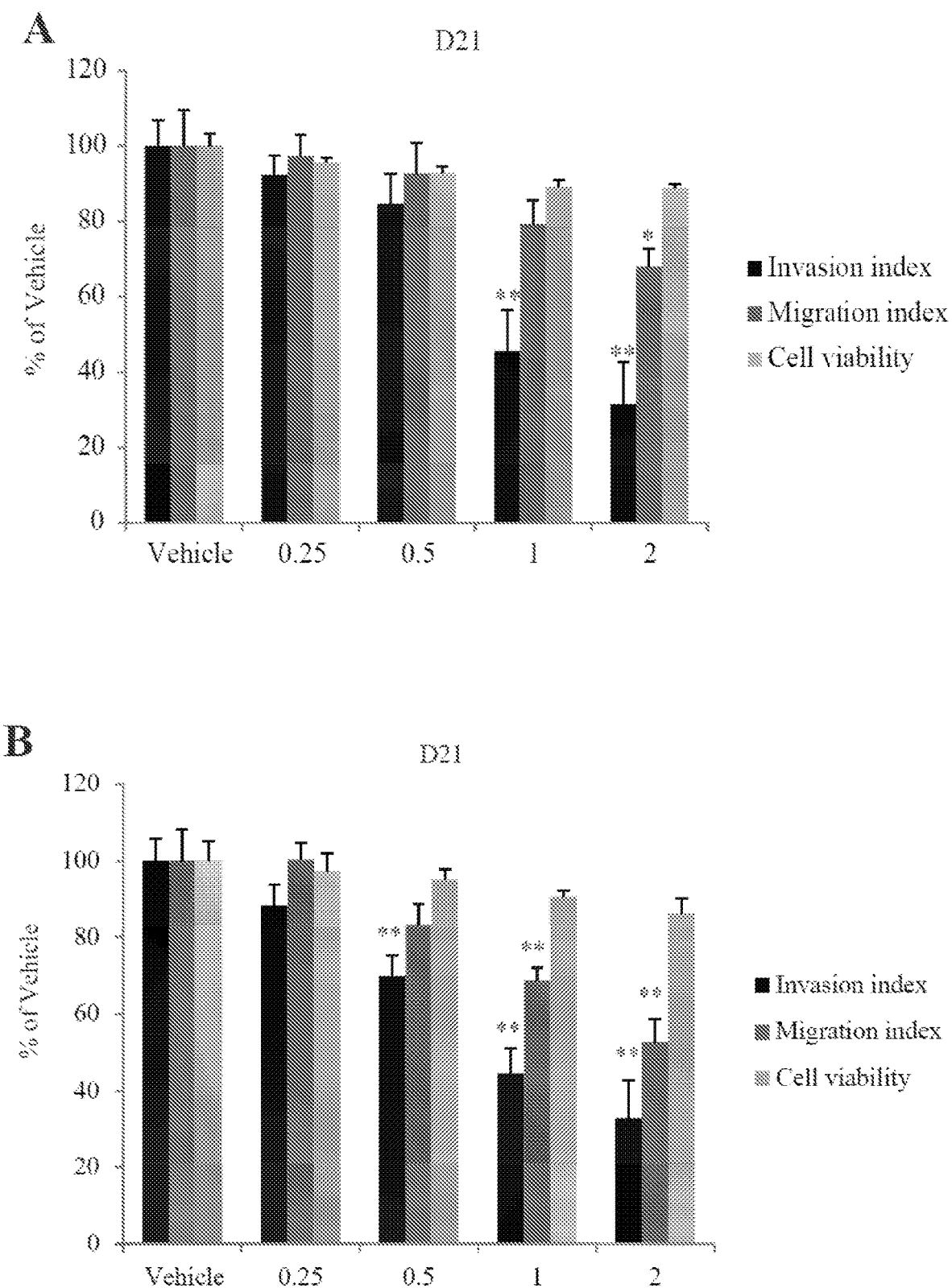
FIG. 11A-B shows data indicating compound 38D-21 inhibits invasion and migration in vitro. A. Effect of compound 38D-21 on cell proliferation, invasion and migration of MDA-MB-231 cells. Cell proliferation was determined by MTT assay, following incubation with the compound. B. Effect of compound 38D-21 on cell proliferation, invasion and migration of MDA-MB-435 cells. Cell proliferation was determined by MTT assay, following incubation with the compound.

Compound 38D-21 was assessed in a cellular model. The moderately and highly metastatic human breast cancer cell lines, MDA-MB-231 and MDA-MB-435, respectively, were used to determine the efficacy of the derivatives toward the inhibition of cancer cell invasion and migration. Cell proliferation assays showed that compound 38D-21 was not cytotoxic to either cell line (FIG. 11). For the invasion assays, breast cancer cells were seeded in matrigel-coated inserts, which were placed above wells containing fetal bovine serum as the chemoattractant and various concentrations of the inhibitor was added to each insert. After the number of invading cells was counted, it was apparent that compound 38D-21 was able to inhibit the invasion in a dose-dependent manner. At 2 µM, 38D-21 inhibited approximately 75% of cell invasion of both breast cancer cell types (FIG. 11). Similarly, 38D-21 was able to inhibit the migration of about 25% of the less metastatic breast cancer cells, MDA-MB-231, whereas it inhibited about 40% of the more detrimental MDA-MB-435 cells from migrating in vitro (FIG. 11). Compound 38D-16 showed similar data. Hence, AEP inhibitors block cell migration and invasion without impinging on the cell viability.

Compound 38D-21 Inhibits Breast Cancer Metastasis In Vivo

The ability of compound 38D-21 to inhibit the metastasis of breast tumor cells in vivo was subsequently examined. A murine model of breast cancer metastasis was developed by subcutaneously injecting MDA-MB-231 cells into the mammary fat pad of nude mice. Compound 38D-21 was administered to the mice via oral gavage at doses of 3 mg/kg or 10 mg/kg or vehicle alone was given to the control group. After 42 days of treatment, the lungs were assessed for the presence of metastatic nodules; 3 mg/kg of compound 38D-21 significantly decreased the number of nodules present on the mice, while the 10 mg/kg dosage almost completely prevented lung metastasis (FIG. 12). There was no significant difference between the mammary tumor weight or volume between the control and drug-treated mice. The percentage of mice with metastatic nodules on their lungs was 100% for the control mice and decreased to 33% for the mice that received the 3 mg/kg dosage and 17% for the mice that received the higher 10 mg/kg dosage (FIG. 12). Although treatment with compound 38D-21 impeded breast cancer metastasis, no significant toxicity was observed, as demonstrated by the similarity in body weight between the control group and the treated mice. Pathological examination of various major organs, such as kidney, liver and bone marrow, did not exhibit any significant amount of toxicity. Moreover, complete blood count (CBC) analysis revealed no significant difference between the drug- and vehicle-treated mice. There is a slight increase in the size of the spleen in the drug-treated mice, fitting with previous observations that knockout of AEP leads to splenomegaly.

Compound 38D-21 Inhibits Cleavage of MMP-2 In Vitro and In Vivo

Since the AEP inhibitor was able to prevent mammary tumor metastasis to the lungs of mice, whether this observation was due to the inhibition of the AEP-mediated cleavage of the matrix metalloproteinase, MMP-2 was tested. The linkage between the overexpression of AEP and the increased invasive and metastatic potential of cancer cells, along with the observation that MMP-2 is a major substrate of AEP, suggests that AEP may exacerbate the migratory potential of tumor tissues through its cleavage of MMP-2. Therefore, gelatin zymography was used to assess whether the inhibition of AEP was concomitant with the inhibition of MMP-2 cleavage and mammary tumor metastasis. Initially, compound 38D-21 was found to inhibit MMP-2 cleavage in the presence of purified active AEP in vitro. As the AEP inhibitor concentration gradually increased, MMP-2 cleavage progressively decreased (FIG. 13A). Similarly, endogenous MMP-2 cleavage was inhibited in a dose-dependent manner in MDA-MD-231 breast cancer cells, however, the cell viability was not affected by the presence of the drug (FIGS. 13B & C). Interestingly, the ratio of cleaved MMP-2 to full-length MMP-2 (pro-MMP-2) was observed to decrease in the mammary tumor tissue of mice treated with 3 mg/kg or 10 mg/kg compound 38D-21 (FIG. 13D). Collectively, this data indicates that compound 38D-21 inhibits AEP, subsequently inhibiting MMP-2 from being cleaved by AEP, resulting in suppression of the metastasis of the mammary tumor cells.

$IC_{50}$ Assays

Various concentrations of the appropriate compound were incubated with AEP reaction buffer (50 mM Sodium Citrate pH 5.5, 0.1% CHAPS, 60 mM $Na_2HPO_4$, 1 mM EDTA, final pH 6.0) and peptide substrate, 10 µM Cbz-Ala-Ala-Asn-AMC (Bachem). The reaction was initiated upon addition of 50 nM AEP and fluorescent product formation was monitored over 15 min. The $IC_{50}$ values were calculated from the following equation: Fractional Enzymatic Activity=1/(1+ ([I]/$IC_{50}$)), in which [I]=Inhibitor concentration and $IC_{50}$=inhibitor concentration that yields half-maximal activity. Data were analyzed with GraFit version 5.0.11 software package.

Inhibition Kinetics Assays

To determine the inhibition constants and the mechanism by which compound 38 inhibits AEP, the steady-state kinetic parameters for the hydrolysis of the peptide substrate, Z-AAN-AMC, were determined in the absence or presence of increasing concentrations of inhibitor. In these assays, specified concentrations of the inhibitor were pre-incubated with substrate for 10 min at 37° C., then 50 nM AEP was added to initiate the reaction, which was quenched after 10 min. The RFU values of the reaction product were converted to micromolar values with an AMC standard curve and the final reaction rates were plotted against substrate concentration and globally fit to equations representative of competitive inhibition (eq 1), noncompetitive inhibition (eq 2), mixed inhibition (eq 3) and uncompetitive inhibition (eq 4) using a nonlinear least fit squares approach by GraFit version 5.0.11.

$$v=V_{max}[S]/([S]+K_m(1+[I]/K_{is})) \quad \text{(eq 1)}$$

$$v=V_{max}[S]/([S](1+[I]/K_i)+K_m(1+[I]/K_i)) \quad \text{(eq 2)}$$

$$v=V_{max}[S]/([S](1+[I]/K_{ii})+K_m(1-[I]/K_{is})) \quad \text{(eq 3)}$$

$$v=V_{max}[S]/([S](1+[I]/K_{ii})+K_m) \quad \text{(eq 4)}$$

In the equations, $K_{ii}$ is the intercept $K_i$, and $K_{is}$ is the slope $K_i$. The mode of the inhibition induced by the compounds on AEP was determined by the best fit of the data to equations 1-4. Visual inspection of the fits, and a comparison of the standard errors, was used to confirm these assignments.

Time Course Inactivation Assays

Progress curves were generated by incubating 5 μM Z-AAN-AMC and the specified concentration of inhibitor in assay buffer at 37° C. for 10 min. The reaction was initiated by the addition of 50 nM AEP and quenched after 10 min. The concentration of the product was determined from an AMC standard curve and the data was fit by nonlinear regression. Since the curves were nonlinear, they were fit to equation 5, using the GraFit version 5.0.11 software package, $$[\text{Product}]=v_i(1-e^{-k_{obs.app}*t})/k_{obs.app} \quad \text{(eq 5)}$$

where $v_i$ is the initial velocity, $k_{obs.app}$ is the apparent pseudo-first order rate constant for inactivation, and t is time. Equation 6, $$k_{obs}=((1+[S])/K_m)k_{obs.app} \quad \text{(eq 6)}$$

was used to correct the apparent pseudo-first-order inactivation rate constants, obtained from this analysis, for substrate concentration and the pseudo-first-order inactivation rate constants, i.e. $k_{obs}$, thus obtained, were plotted against the tested inhibitor concentrations. As the data are consistent with a two-step mechanism of inactivation, they were fit to equation 7, $$k_{obs}=(k_{inact}[I])/(K_I+[I]) \quad \text{(eq 7)}$$

using the GraFit version 5.0.11 software, where $K_I$ is the concentration of inactivator that yields half-maximal inactivation, $k_{inact}$ is the maximal rate of inactivation, and [I] is the concentration of inactivator.

Cell Viability Assay

Cells were seeded and cultured in 96-well plates (4000 cells/well). The next day, the medium was replaced with fresh medium containing different concentrations of the drugs or vehicle controls. The cells were then incubated at 37° C. for the indicated times. After treatment, the cells were incubated for another four hours with 0.5 mg/ml MTT solution at 37° C. The culture medium was discarded, and 0.1 ml DMSO was used to dissolve precipitate. The absorbance was measured at 570 nm using an Automated Microplated Reader (Synergy 2, BioTek, VT, USA).

Chamber Invasion and Migration Assay

Invasion of cells through Matrigel was determined using a Transwell system (10 mm diameter, 8-μm pore size with polycarbonate membrane; Corning Costar). Briefly, cells ($3 \times 10^4$) were suspended in serum free medium with different concentrations of drug and seeded onto Matrigel-coated transwell chamber. Medium with 5% serum was used as a chemoattractant in the lower chambers. After desired times of incubation at 37° C. under 5% $CO_2$/95% air atmosphere, medium was aspirated, and cells on the upper side of the membrane were removed with a cotton swab. The invading cells on the bottom of the filter were stained with 0.5% crystal violet in 25% methanol and quantified under invert microscope. In the transwell chamber migration assay, the BD Falcon Cell Culture Insert System containing membranes with 8 μm pore size was utilized in the assay; $1.5 \times 10^4$ cells were suspended in serum free medium with different concentrations of drug and seeded onto 10-mm upper chamber of transwell system. Medium with 5% serum and same concentrations of drugs in corresponding upper chambers was added to the lower chamber. After a fixed time of incubation, the migration cells were stained and quantified as in the invasion assay.

In Vivo Spontaneous Metastasis Assay

MDA-MB-231 cells were trypsinized and resuspended in serum free media at a density of $1 \times 10^7$/ml and implanted into the mammary fat pad of the mice (200 μl/mouse). When the volumes of xenografts reached to 100 $mm^3$, mice were randomized to receive vehicle control (12 mice per group) or tested compounds (six mice per group). Test compound or vehicle was then administered orally for 42 consecutive days. Tumor volume in $mm^3$ was determined using the formula (length×$width^2$)/2, where length was the longest axis and width being the measurement at right angles to the length. Twenty-four hours after the last drug administration, the animals were sacrificed and tumors/organs were collected for various experiments. For lung metastasis, after the mice were killed, the lungs were removed, washed, and fixed with Bouin's solution for 24 hr and the number of the tumor nodules on the whole surface of the lungs was counted under a dissecting microscope. Sections of the lungs were stained with hematoxylin and eosin (HE) to confirm the formation of metastases.

Gelatin Zymography Assays

Gelatinase-containing samples were dissolved in Laemmli sample buffer in the absence of reducing agents and electrophoresed in 8% polyacrylamide SDS gels co-polymerized with gelatin (1 mg/ml). Following electrophoresis, the gels were washed twice (30 min each time) and once in calcium assay buffer (40 mM Tris, 0.2 M NaCl, 10 mM $CaCl_2$, pH 7.5), and then incubated in the calcium assay buffer at 37° C. for certain times with gently shaking. Gels were then fixed in 45% methanol/10% glacial acidic acid containing 0.5% Commassie Blue G-250 for 1 hr followed by destaining with 10% acetic acid, 10% methanol. Enzymedigested regions were observed as white bands against a blue background. Zones of enzymatic activity were seen as negatively stained bands.

What is claimed:

1. A pharmaceutical composition comprising 7-(3-(4-chlorophenoxy)-2-hydroxypropyl)-8-mercapto-3-methyl-3,7-dihydro-1H-purine-2,6-dione or salts thereof and a pharmaceutically acceptable excipient.

2. The pharmaceutical composition of claim 1 in the form of a pill, capsule, or tablet.

3. The pharmaceutical composition of claim 1, wherein the pharmaceutically acceptable excipient is selected from a saccharide, disaccharide, sucrose, lactose, glucose, mannitol, sorbitol, polysaccharides, starch, cellulose, microcrystalline cellulose, cellulose ether, hydroxypropyl cellulose (HPC), xylitol, sorbitol, maltito, gelatin, polyvinylpyrrolidone (PVP), polyethylene glycol (PEG), hydroxypropyl methylcellulose (HPMC), crosslinked sodium carboxymethyl cellulose, dibasic calcium phosphate, calcium carbonate, stearic acid, magnesium stearate, talc, magnesium carbonate, silica, vitamin A, vitamin E, vitamin C, retinyl palmitate, selenium, cysteine, methionine, citric acid, and sodium citrate, methyl paraben, propyl paraben, and combinations thereof.

* * * * *